(12) United States Patent
Kawashima et al.

(10) Patent No.: US 9,575,097 B2
(45) Date of Patent: Feb. 21, 2017

(54) SPECIMEN AND CURRENT MEASURING METHOD

(71) Applicant: Fuji Jukogyo Kabushiki Kaisha, Tokyo (JP)

(72) Inventors: Ai Kawashima, Tokyo (JP); Hiroyasu Fujita, Tokyo (JP); Naoyuki Sekine, Tokyo (JP)

(73) Assignee: FUJI JUKOGYO KABUSHIKI KAISHA, Tokyo (JP)

( * ) Notice: Subject to any disclaimer, the term of this patent is extended or adjusted under 35 U.S.C. 154(b) by 158 days.

(21) Appl. No.: 14/543,112

(22) Filed: Nov. 17, 2014

(65) Prior Publication Data

US 2015/0137802 A1     May 21, 2015

(30) Foreign Application Priority Data

Nov. 18, 2013  (JP) ................................. 2013-237927
Mar. 28, 2014  (JP) ................................. 2014-068034
Aug. 27, 2014  (JP) ................................. 2014-172183

(51) Int. Cl.
*G01R 19/00*       (2006.01)
*B32B 5/22*        (2006.01)
(Continued)

(52) U.S. Cl.
CPC .............. *G01R 19/0092* (2013.01); *B32B 3/08* (2013.01); *B32B 3/266* (2013.01); *B32B 5/22* (2013.01);
(Continued)

(58) Field of Classification Search
CPC ....... G01R 31/008; G01R 31/00; G01R 19/10; B32B 37/06; B32B 15/04; B32B 37/10
See application file for complete search history.

(56) References Cited

U.S. PATENT DOCUMENTS

2004/0185733 A1*  9/2004  Murai ..................... B29C 70/22
                                              442/265
2009/0102486 A1*  4/2009  Purdy ................ G01R 31/1227
                                              324/455
(Continued)

FOREIGN PATENT DOCUMENTS

JP     H 05-269874 A    10/1993
JP     2002-225166 A     8/2002
(Continued)

OTHER PUBLICATIONS

JPO Notification of Reasons for Refusal dated Oct. 6, 2015 and Decision of Grant dated Jan. 5, 2016.

*Primary Examiner* — Vinh Nguyen
*Assistant Examiner* — Alvaro Fortich
(74) *Attorney, Agent, or Firm* — McGinn IP Law Group, PLLC.

(57) ABSTRACT

Composite material sheets containing conductive fibers are laminated, and release films are interposed between the sheets so as to extend from one end to the center of the sheets. The sheets are heated under pressure to shape a composite material. Discrete conductive wires through which a measurement current is passed are connected to end surfaces of the respective layers in the composite material on the side on which the release films are interposed. A common conductive wire through which the measurement current is passed is connected to a surface of one of an uppermost layer and a lowermost layer at an end of the composite material opposite to the side on which the release films are interposed. A current is passed between the common conductive wire and the discrete conductive wires. Currents in the respective layers are sequentially or simultaneously measured using an ammeter.

20 Claims, 25 Drawing Sheets

(51) Int. Cl.
    *B32B 5/24*     (2006.01)
    *B32B 5/26*     (2006.01)
    *B32B 5/28*     (2006.01)
    *B32B 27/04*    (2006.01)
    *B32B 27/12*    (2006.01)
    *G01R 15/18*    (2006.01)
    *G01R 19/10*    (2006.01)
    *G01R 31/00*    (2006.01)
    *B32B 3/08*     (2006.01)
    *B32B 3/26*     (2006.01)
    *B64F 5/00*     (2006.01)
    *G01N 27/04*    (2006.01)

(52) U.S. Cl.
    CPC . *B32B 5/24* (2013.01); *B32B 5/26* (2013.01); *B32B 5/28* (2013.01); *B32B 27/04* (2013.01); *B32B 27/12* (2013.01); *G01R 15/181* (2013.01); *G01R 19/10* (2013.01); *G01R 31/008* (2013.01); *B32B 2250/03* (2013.01); *B32B 2250/05* (2013.01); *B32B 2250/24* (2013.01); *B32B 2250/40* (2013.01); *B32B 2250/42* (2013.01); *B32B 2250/44* (2013.01); *B32B 2260/021* (2013.01); *B32B 2260/023* (2013.01); *B32B 2260/046* (2013.01); *B32B 2262/106* (2013.01); *B32B 2307/202* (2013.01); *B32B 2457/00* (2013.01); *B32B 2605/18* (2013.01); *B64F 5/0045* (2013.01); *G01N 27/045* (2013.01)

(56) References Cited

U.S. PATENT DOCUMENTS

| | | | | |
|---|---|---|---|---|
| 2010/0319171 | A1* | 12/2010 | Yu | E04C 5/085 26/71 |
| 2011/0222225 | A1* | 9/2011 | Kessler | G06F 3/05 361/679.02 |
| 2012/0223720 | A1* | 9/2012 | Landes | B64F 5/0045 324/533 |
| 2013/0008700 | A1* | 1/2013 | Osuga | H05K 1/0243 174/258 |
| 2013/0118644 | A1* | 5/2013 | Tanaka | C23C 8/36 148/241 |
| 2013/0200904 | A1* | 8/2013 | Millet | G01R 31/11 324/533 |
| 2013/0276574 | A1* | 10/2013 | Uhl | F16C 7/026 74/579 R |

FOREIGN PATENT DOCUMENTS

| | | |
|---|---|---|
| JP | 2013-035858 A | 2/2013 |
| JP | 2013-050306 A | 3/2013 |
| JP | 2013-053858 A | 3/2013 |
| JP | 2013-508722 A | 3/2013 |
| WO | WO 2011/049801 A1 | 4/2011 |

* cited by examiner

FIG. 4A
SAMPLE A

M  FIBER ARRANGEMENT DIRECTION

| P1 | L1 | | 0° |
| P2 | L2 | | 0° |
| P3 | L3 | | 0° |
| P4 | L4 | | 0° |
| P5 | L5 | | 0° |
| P6 | L6 | | 0° |
| P7 | L7 | | 0° |
| P8 | L8 | | 0° |

FIG. 4B
SAMPLE B

M  FIBER ARRANGEMENT DIRECTION

| P1 | L1 | 0° |
| | L2 | 90° |
| P2 | L3 | 0° |
| | L4 | 90° |
| P3 | L5 | 90° |
| | L6 | 0° |
| P4 | L7 | 90° |
| | L8 | 0° |

SAMPLE A

SAMPLE B

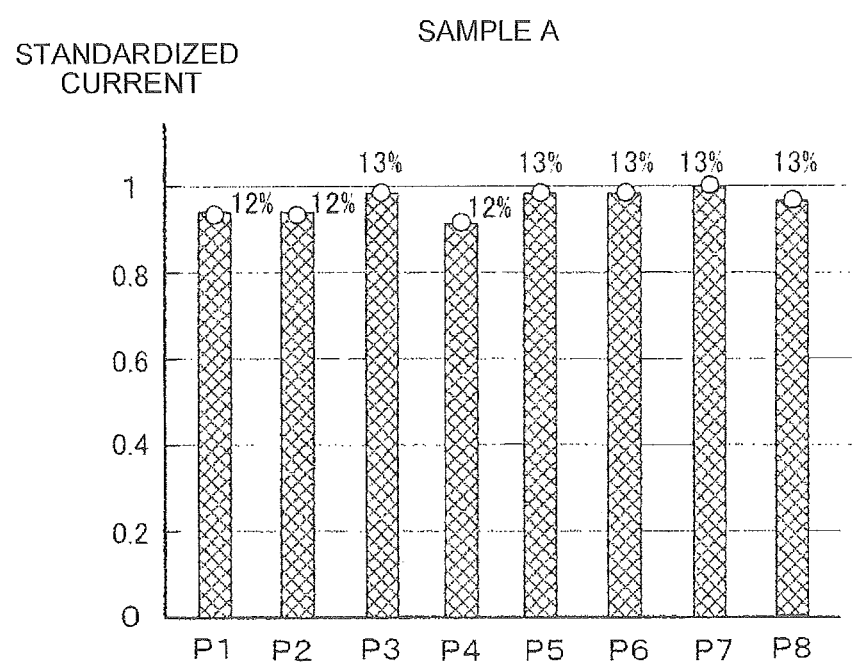

FIG. 18A
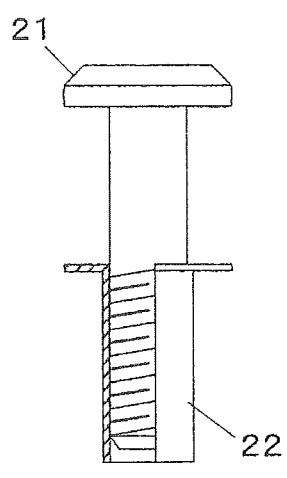
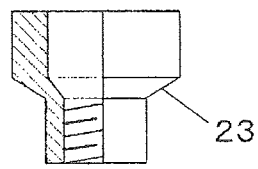
FIG. 18B
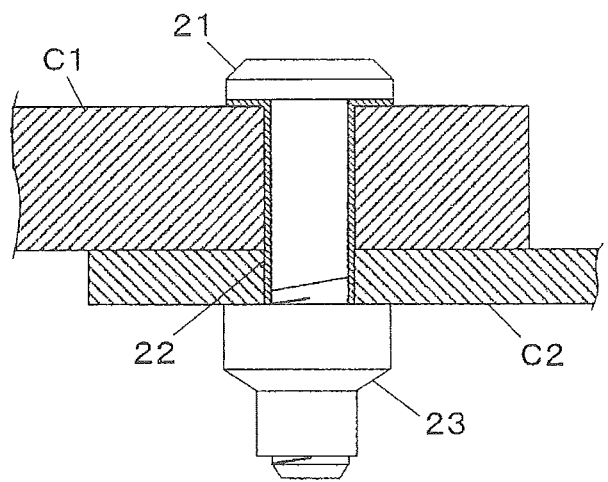

FIG. 19A

| | | C2 | FIBER ARRANGEMENT DIRECTION |
|---|---|---|---|
| P1 | L1 | | 0° |
| P2 | L2 | | 0° |
| P3 | L3 | | 0° |
| P4 | L4 | | 0° |
| P5 | L5 | | 0° |
| P6 | L6 | | 0° |
| P7 | L7 | | 0° |
| P8 | L8 | | 0° |

FIG. 19B

| | | C2 | FIBER ARRANGEMENT DIRECTION |
|---|---|---|---|
| P1 | L1 | | 0° |
| | L2 | | 90° |
| P2 | L3 | | 0° |
| | L4 | | 90° |
| P3 | L5 | | 90° |
| | L6 | | 0° |
| P4 | L7 | | 90° |
| | L8 | | 0° |

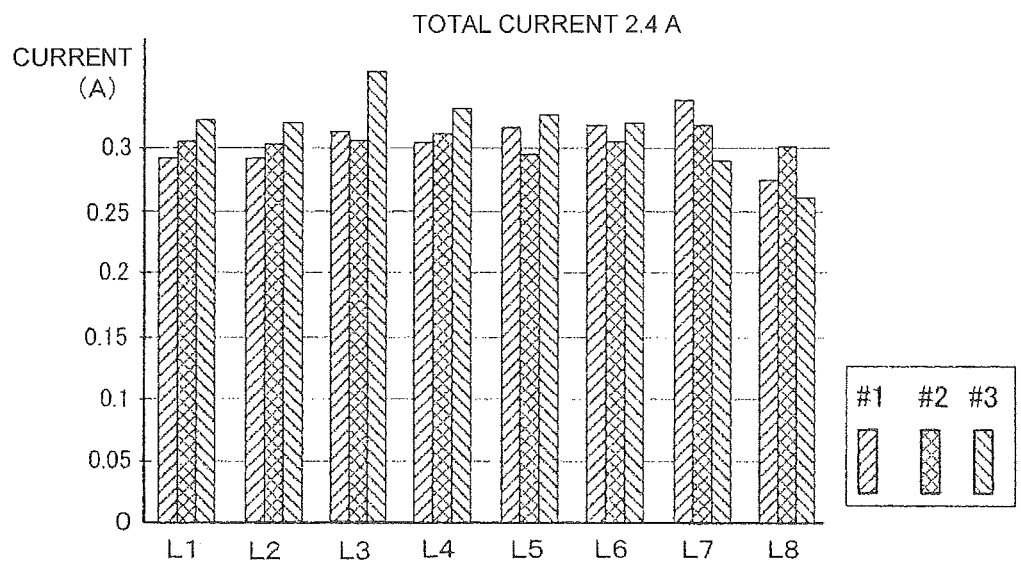
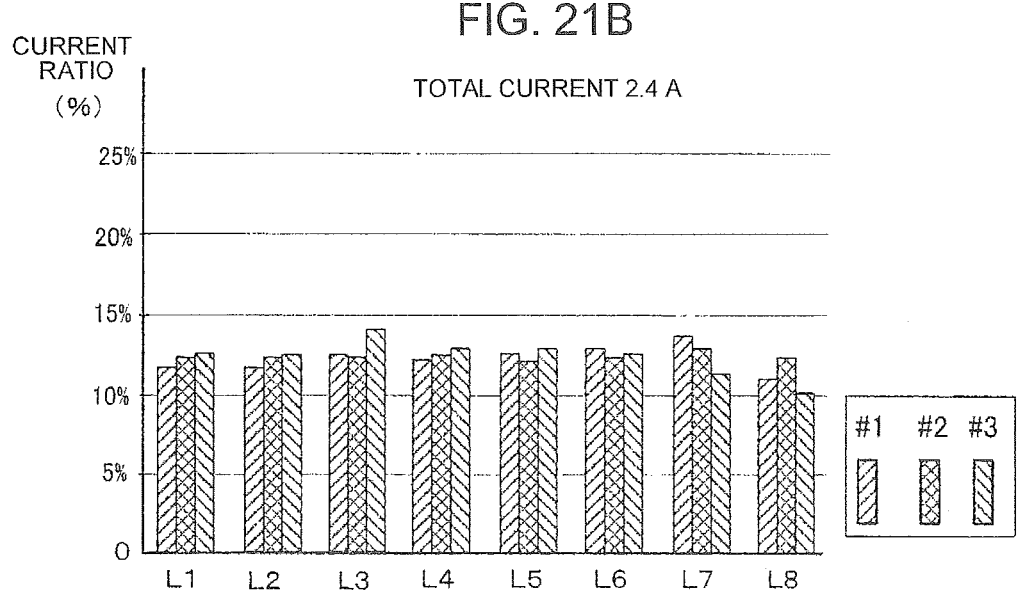

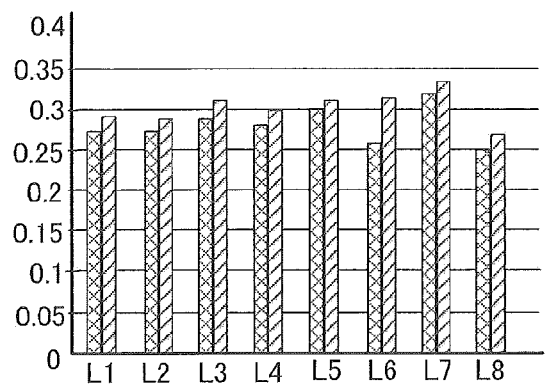
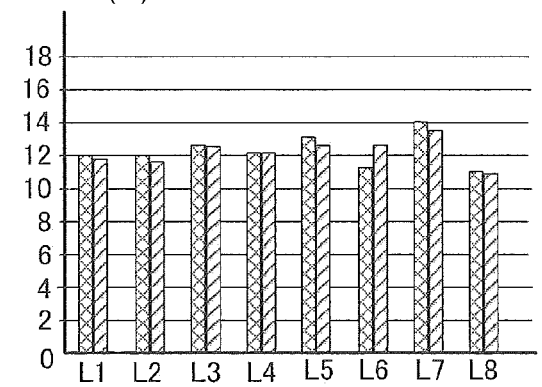
FIG. 22A #1
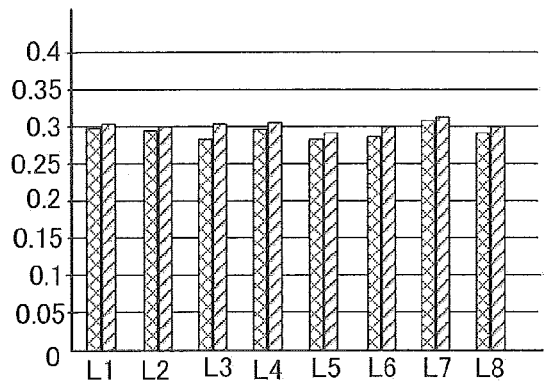
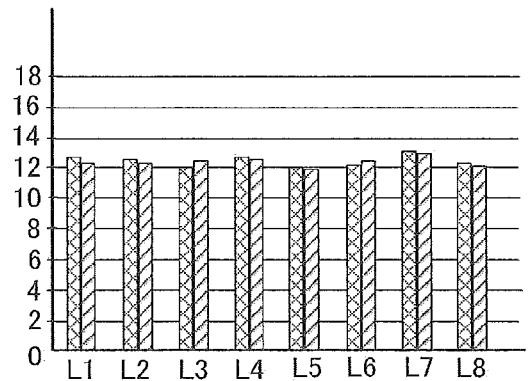
FIG. 22B #2
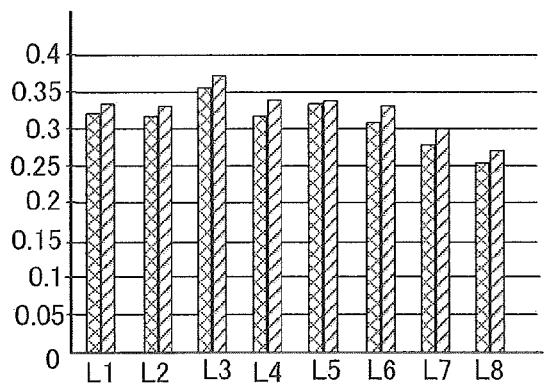
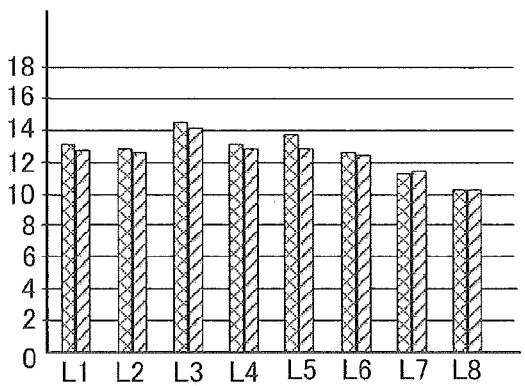
FIG. 22C #3

SPECIMEN AND CURRENT MEASURING METHOD

CROSS-REFERENCE TO RELATED APPLICATIONS

The present application claims priority from Japanese Patent Application Nos. 2013-237927 filed on Nov. 18, 2013, 2014-068034 filed on Mar. 28, 2014 and 2014-172183 filed on Aug. 27, 2014, the entire contents of which are hereby incorporated by reference.

BACKGROUND

1. Technical Field

The present invention relates to a specimen used to measure a current flowing through a composite material containing conductive fibers and a current measuring method for the specimen.

2. Related Art

In recent years, the application of composite materials such as carbon fiber reinforced plastic (CFRP) to structures has been spreading widely. For example, such composite materials have been applied in a variety of fields, for example, to fuselages of airplanes, frameworks of automobiles, and blades of windmills. On the other hand, the composite material contains conductive fibers such as carbon fibers, and may thus serve as an unintended current path in connection with the design of the structure when a short circuit or lightning strike occurs. For example, in airplanes, fuel may be ignited by a possible spark caused by a lightning stroke. Accordingly, clarifying the current distribution in the fuselage during lightning is important.

However, the composite material, particularly a composite material containing conductive fibers such as carbon fiber reinforced plastic (CFRP), contains carbon fibers, which are electrically conductive, and a resin, which is an insulator, and is thus easily affected by a fiber arrangement direction. Thus, the composite material involves a more complicated current path than metallic materials. A particularly complicated current path is involved in a carbon fiber laminate in which a plurality of layers with different fiber directions is laminated. This leads to the need for a technique that allows more accurate measurement of a current flowing through the composite material.

For example, conventional inventions that allow measurement of the behavior or magnitude of a current flowing through the composite material are disclosed in Japanese Unexamined Patent Application Publication (JP-A) No. 2013-050306 and Japanese Unexamined Patent Application Publication (JP-A) No. 2013-053858. The invention disclosed in JP-A No. 2013-050306 enables visualization of local discharge when a current is passed through a composite material with a fastener. Furthermore, the invention disclosed in JP-A No. 2013-053858 enables measurement of a current in a carbon fiber laminate in which a plurality of layers of fibers in different directions is laminated.

The invention disclosed in JP-A No. 2013-050306 enables visualization of local discharge. Furthermore, the current measurement in the invention disclosed in JP-A No. 2013-053858 enables the distribution of currents in an in-plane direction in the composite material to be determined. However, in these inventions, it is not possible to measure a current in an out-of-plane direction that crosses the surface of in a laminate composite material. Additionally, a propagation mechanism for a current in an out-of-plane direction in the laminate composite material has not been theoretically clarified.

Moreover, both JP-A No. 2013-050306 and JP-A No. 2013-053858 disclose an example of current measurement in a specimen with a fastener. However, both JP-A No. 2013-050306 and JP-A No. 2013-053858 involve a specimen that is a single laminate composite material and fail to disclose an example of current measurement intended to clarify a propagation mechanism for a current in a specimen of two laminate composite materials coupled together with a fastener or conditions for a preferred coupling area.

Measures allowing smooth flow of a lightening current resulting from a lightning stroke and charge of static electricity are taken for an airplane structure to which a laminate composite material (composite material) is applied. This prevents thermal destruction of the structure resulting from application of a current to the structure and ignition in a fuel tank caused by discharge. In particular, for a lightning resistance measure, the fastener between the composite materials is desirably a bolt that offers reduced contact resistance to a base material to allow electricity to flow smoothly. However, conventionally available fasteners are special products and expensive, resulting in having an impact on fuselage manufacturing costs.

On the other hand, less expensive fasteners are also available, but when such fasteners are used without any modification, the fasteners may cause discharge because these fasteners offer large contact resistance to the composite material. Thus, the fasteners need a separate discharge measure. The large contact resistance is assumed to be ascribed to a difference in diameter between the bolt and a machined hole, a difference in fastener configuration, or a difference in a state of contact between the fastener and the machined hole resulting from different machining conditions.

SUMMARY OF THE INVENTION

With the foregoing in view, it is an object of the present invention to provide a specimen that allows measurement of a current flowing through each layer in a laminate composite material and a current measuring method for the specimen.

It is another object of the present invention to provide a specimen that allows determination of the form and size of a fastener and machining conditions for the fastener all of which are effective for preventing discharge from the fastener, and a current measuring method for the specimen.

To accomplish the above-described objects, a first aspect of the present invention provides a specimen including multiple composite material sheets that are laminated together and containing conductive fibers. Spacing elements that space the composite material sheets from one another are provided between the composite material sheets at an end of the specimen.

The specimen may further include a common conductive wire connector to which a common conductive wire allowing a current to be applied to the specimen is electrically connected at a part of the specimen where the composite material sheets are not spaced from one another.

The common conductive wire connector may be a part of a surface layer of the specimen from which the conductive fibers in the composite material sheet are externally exposed.

The common conductive wire connector may be an end of the specimen where the composite material sheets are not spaced from one another.

The specimen may further include a through-hole that penetrates the composite material sheets in a laminate direction. The common conductive wire connector may be a conductive element that is inserted into the through-hole.

The specimen may further include at least one first composite material and at least one second composite material that each includes the composite material sheets laminated together, and are laid on top of each other and coupled together with a conductor that penetrates both composite materials. The second composite material may include the spacing elements.

A discrete conductive wire may be enabled to be connected to each of the spaced composite material sheets on the composite material sheet spacing side of the second composite material.

The first composite material may include a common conductive wire connector to which a common conductive wire is electrically connected, the common conductive wire which allows a current to be applied to the specimen.

The first composite material may include through-holes at predetermined intervals along a periphery of the first composite material, and conductive elements inserted respectively into the through-holes enables connection of one or more of the second composite materials.

The conductive element may be a fastener that fastens the specimen to another element.

The spacing element may be a release film having an insulating property.

A second aspect of the present invention provides a specimen current measuring method for measuring a current flowing through the specimen described above. The method includes: electrically connecting a common conductive wire that allows a measurement current to be input, to the specimen; electrically connecting discrete conductive wires that allow the measurement current to be picked up to the respective composite material sheets spaced from one another by the spacing elements or to some of the composite material sheets; and passing a current between the common conductive wire and the discrete conductive wires to allow either one of discrete measurement and simultaneous measurement of currents flowing through the composite material sheets in the specimen.

Conductive fibers in the composite material sheet in a surface layer of the specimen may be externally exposed, and the common conductive wire may be connected to the exposed part.

A through-hole that penetrates the composite material sheets in a lamination direction may be formed in the specimen, and the common conductive wire may be connected to a conductive element inserted into the specimen.

The conductive element may be a fastener that fastens the specimen to another element.

The common conductive wire may be connected to an end of the specimen.

A third aspect of the present invention provides another specimen current measuring method for measuring a current flowing through the specimen described above. The method includes: electrically connecting a common conductive wire that allows a measurement current to be input, to the first composite material; electrically connecting discrete conductive wires that allow the measurement current to be picked up to the respective composite material sheets spaced from one another by the spacing elements or to some of the composite material sheets; and passing a current between the common conductive wire and the discrete conductive wires to allow either one of discrete measurement and simultaneous measurement of currents flowing through the composite material sheets in the second composite material.

The current flowing through each of the composite material sheets may be measured based on either one of a current flowing through the corresponding discrete conductive wire and a voltage within a predetermined range of the discrete conductive wire.

BRIEF DESCRIPTION OF THE DRAWINGS

FIG. 4A and FIG. 4B are diagrams illustrating examples of structures of two specimens produced for experiments conducted to verify the effects of the first implementation and fiber arrangement directions in CFRP layers in the specimens;

FIG. 12 is a diagram illustrating the results of current measurement, with the common conductive wire being connected, of the CFRP layers provided with an electrode on the end surface of the specimen;

FIG. 18A and FIG. 18B are each a partly cross-sectional enlarged diagram illustrating details of a fastener (bolt) used for the specimen according to the second implementation illustrated in FIG. 2 and details of a coupling area where two composite material plates are coupled together using the fastener;

FIG. 19A is a diagram illustrating an example of structure of composite material plates providing a specimen produced for experiments conducted to verify the effects of the second implementation and fiber arrangement directions in CFRP layers in the specimen, and FIG. 19B is a diagram illustrating an example of another structure of composite material plates and fiber arrangement directions in CFRP layers;

FIG. 21A and FIG. 21B are graphs illustrating the results of current measurement and the ratios of currents, respectively, for CFRP layers in three specimens produced according to the second embodiment;

FIG. 22A, FIG. 22B, and FIG. 22C are graphs illustrating the results of current measurement and the ratios of currents for the CFRP layers in the three specimens produced according to the second embodiment, with the position of an electrode varied to which a current is applied;

DETAILED DESCRIPTION

Implementations of a specimen of a laminate composite material and a current measuring method according to the present invention will be described below with reference to the drawings.

(First Implementation)

FIG. 1 is a laminate composite material and a specimen (test piece) of the laminate composite material to which a current measuring method according to the first implementation is applied.

Figure 1A:
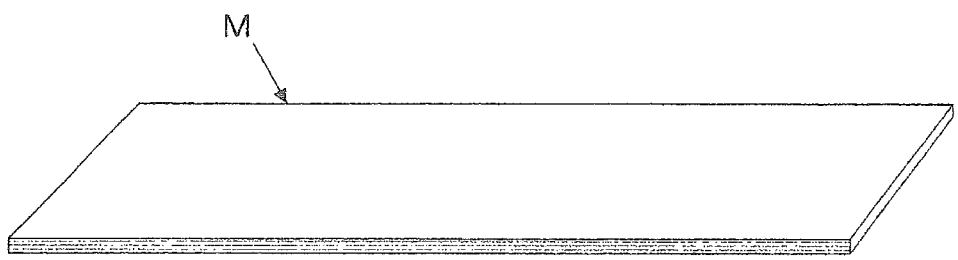
FIG. 1A and FIG. 1B are diagrams illustrating a laminate composite material and a specimen (test piece) thereof to which a current measuring method according to a first implementation is applied.

The composite material to be measured is fiber reinforced plastic including a resin reinforced with fibers, and is carbon fiber reinforced plastic (CFRP) containing carbon fibers. As illustrated in FIG. 1A, a specimen M is a shaped like a strip.

Figure 1B:
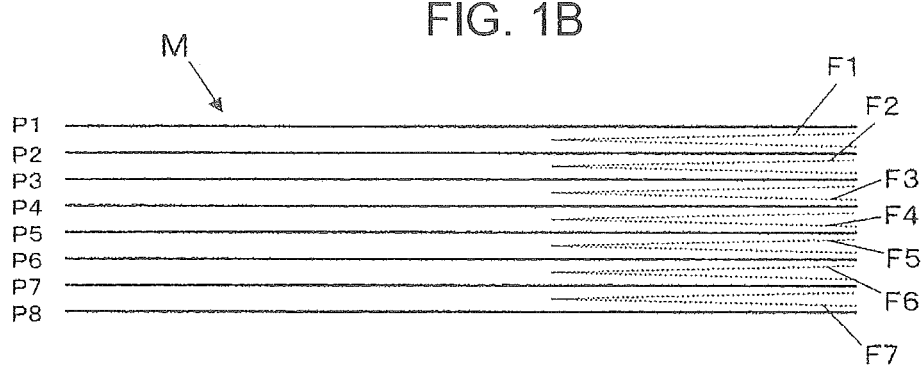

Furthermore, as illustrated in FIG. 1B, the specimen M is a laminated composite material formed by laminating eight prepregs P1 to P8 serving as the composite material sheets of the present invention and each including a plurality of carbon fiber bundles arranged along a predetermined direction and impregnated with an uncured resin. Each of the prepregs P1 to P8 is 1 mm or less (for example, 0.2 mm) in thickness. Additionally, the carbon fibers in each of the layers in the prepregs P1 to P8 are arranged in any direction. The direction is selected so as to correspond to the structure of an actual composite material considered to be used for airplanes and the like. The number of prepregs laminated together is optionally selected so as to correspond to the structure of the actual composite material.

Moreover, the specimen M according to the first implementation includes spacing elements each disposed between the prepreg layers and extending from an end (an end on the right side in the figure) of the specimen M toward the center thereof. For example, as illustrated in FIG. 1B, films (hereinafter referred to as release films) F1 to F7 with the opposite surfaces thereof subjected to a release facilitating treatment are each interposed between the layers so as to extend over a predetermined length from one end to the middle of the specimen M in a longitudinal direction. Furthermore, in the first implementation, each of the release films F1 to F7 is folded in the middle before being inserted between the layers. This structure is used to prevent a situation where, when the release film is a single film that is not folded in the middle, the film may stick to the surfaces of the prepregs to make separation of the adjacent prepreg layers difficult when the release facilitating treatment is uneven. However, the release film is not limited to the folded film that is folded in the middle but may be a single film that is not folded in the middle.

A material for the release film may desirably be a heat-resistant insulating material, for example, Kapton (registered trademark), a type of polyimide rein. The release facilitating treatment executed on the surface of the release film involves, for example, coating of Frekote (registered trademark) as a release agent. The coated release agent is not limited to Frekote but may be any heat-resistant insulating material. The spacing element is not limited to the release film but may be an insulating material such as a silicone rubber sheet or a metallic sheet or the like with a release agent coated thereon. Furthermore, the spacing element is not limited to the thin sheet-like element but may be a wedge- or plate-like resin or a metallic jig with a release agent coated on the surface thereof.

As described above, the CFRP specimen is manufactured by heating, under pressure, the laminated prepregs P1 to P8, with the spacing elements, such as the release films, being interposed between the prepreg layers on one side thereof, whereby the resin is cured. Subsequently, the specimen is completed by connecting a conductive wire through which a measurement current flows to a release side end of each of the CFRP layers. In the first implementation, after the specimen is complete, the release films are released for tests. However, the release films may remain interposed between the layers. When used as the spacing elements, metallic sheets are preferably removed after the specimen is complete.

When the spacing elements are removed, insulating elements are preferably inserted between the layers in order to ensure insulation between the layers during measurement.

A method for manufacturing a specimen is not limited to the method of laminating a plurality of prepregs together and curing the resin as described above. Another method such as an RTM method may be used for manufacturing. For example, a VaRTM method, a type of the RTM method, is a shaping method of arranging a plurality of carbon fiber bundles along a predetermined direction, wrapping the entire carbon fiber bundles with a bag film, vacuumizing the wrapped carbon fiber bundles, injecting a liquid resin into the carbon fiber bundles to impregnate the fibers with the resin, and then using an oven to heat the carbon fiber bundles impregnated with the resin to cure the resin. To manufacture a specimen with the above-described structure using the VaRTM method, the following procedure may be taken. A plurality of carbon fiber bundles is arranged along a predetermined direction. On one side of the bundles, spacing elements such as a plurality of release films are interposed among the carbon fiber bundles at predetermined intervals. The carbon fiber bundles are entirely wrapped with a bag film. The wrapped carbon fiber bundles are vacuumized. A liquid resin is injected into the vacuumized carbon fiber bundles.

Furthermore, the method for manufacturing a specimen may be a technique based on cold curing such as wet layup. In this case, the spacing elements need not exhibit heat resistance, and thus any of a wide variety of spacing elements may be selected for this purpose.

FIG. 2 illustrates an example of connection of a conductive wire to each CFRP layer (composite material sheet) in the specimen. Before the conductive wire is connected, a sanding treatment is executed on the end of each CFRP layer Li so that the resin at the end of each CFRP layer Li is, for example, filed off to expose the carbon fibers. Furthermore, the area subjected to the sanding treatment is preferably further plated. The plating is preferably two-step plating. Moreover, before the plating, the area is preferably pretreated by applying a treatment liquid such as sulfuric acid to the area. To expose the carbon fibers, any measure other than the sanding treatment may be used such as dissolution and decomposition of the resin using a chemical.

Figure 2A:
FIG. 2A and FIG. 2B are each a diagram illustrating an example of connection of conductive wires to respective CFRP layers in the specimen.
Figure 2B:
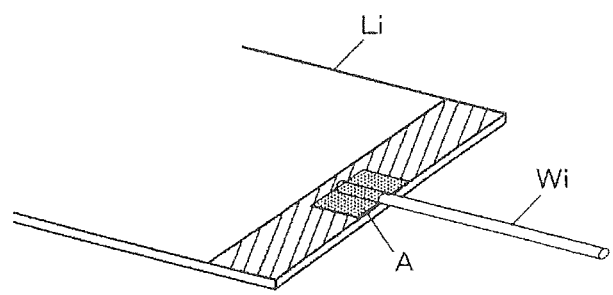

FIG. 2A illustrates that a clip electrode (terminal) Ti is connected to an end of the CFRP layer Li and that a conductive wire Wi is connected to the electrode Ti by soldering or the like. FIG. 2B illustrates that the conductive wire Wi is connected directly to the end of the CFRP layer Li by bringing an end of the conductive wire Wi into contact with the end of the CFRP layer Li, coating a conductive silver paste A on the conductive wire, and heating and sintering the silver paste A. A hatched area in FIG. 2B is the area subjected to the sanding treatment.

Now, a configuration of a current measuring apparatus and a current measuring method, using the specimen of the above-described laminate composite material will be described.

Figure 3A:
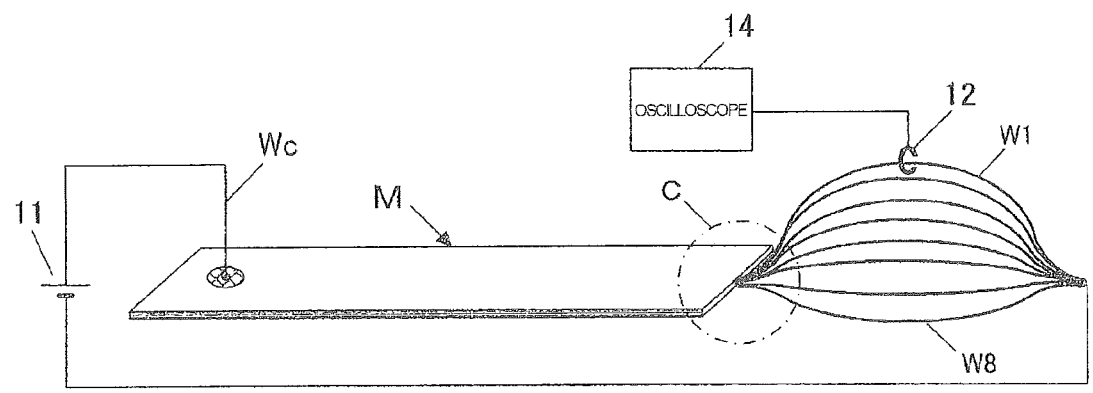
FIG. 3A and FIG. 3B are each a diagram illustrating a method for measuring a current flowing through each of the CFRP layers in the specimen.
Figure 3B:
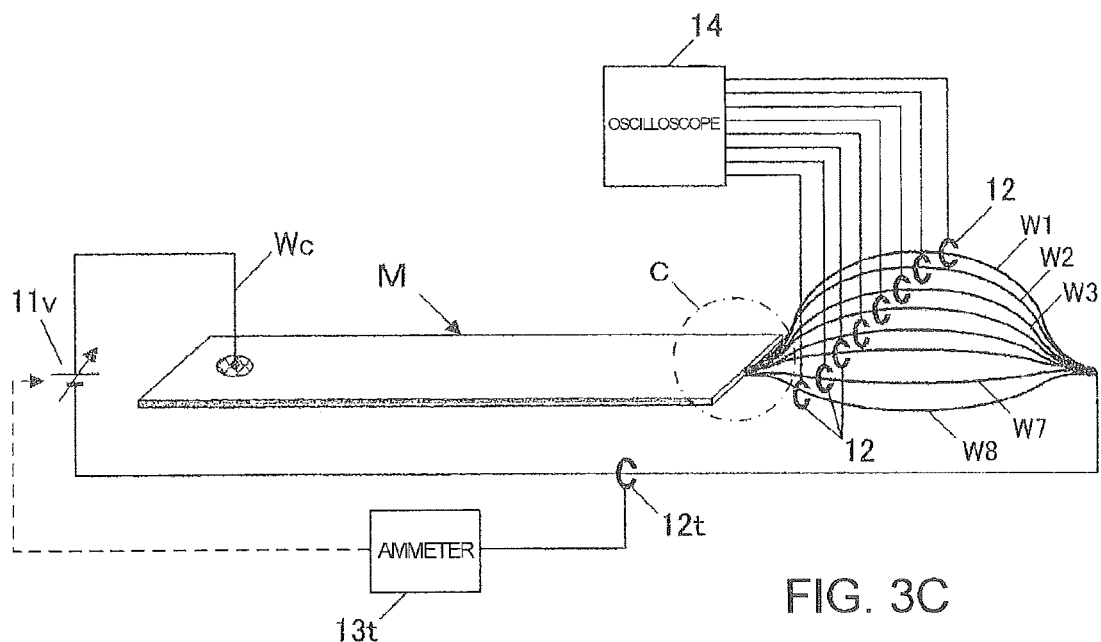
Figure 3C:
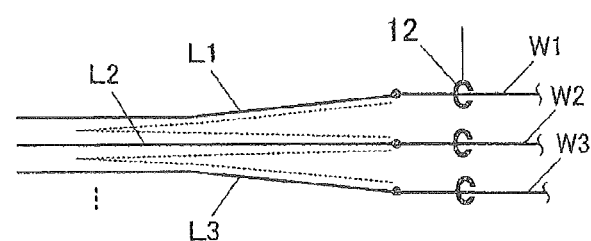
FIG. 3C is an enlarged diagram of a part of FIG. 3A and FIG. 3B which is enclosed by an alternate long and short dash line.

FIGS. 3A to 3C schematically illustrates the current measuring apparatus intended for the specimen M. As illustrated in FIGS. 3A and 3B, the current measuring apparatus includes a DC power supply 11, a Rogowski coil 12 that allows detection of a current flowing through the conductive wire Wi connected to the end of each CFRP layer Li in the specimen, and an oscilloscope 14 connected to the Rogowski coil 12. To check how a current flows when a current waveform (for example, a waveform conforming with the standard specification SAE ARP 5412 for a lightening waveform for airplanes) similar to a lightning current is applied to the specimen, the Rogowski coil 12 corresponding to the frequency band of the lightning waveform may be connected to the oscilloscope 14.

FIG. 3A illustrates that a current flowing through the CFRP layer Li in the specimen M is measured on a layer-by-layer basis. Currents are sequentially measured, with a conductive wire, on which the Rogowski coil 12 is disposed, being selected. FIG. 3B illustrates that currents flowing through all the CFRP layers L1 to L8 in the specimen M can be simultaneously measured. The Rogowski coil 12 is disposed on each of the conductive wires W1 to W8. FIG. 3C is an enlarged diagram of a part of FIG. 3A and FIG. 3B which is enclosed by an alternate long and short dash line C. The conductive wires W1, W2, W3, . . . , are connected to the ends of the respective CFRP layers L1, L2, L3, . . . which are separated from one another.

The Rogowski coil is an annular coil that enables a large current to be measured, and when disposed to surround a measurement point, enables the current to be measured based on voltages induced at the opposite ends of the coil. The current detection element is not limited to the Rogowski coil but may be any other current sensor. Alternatively, a resistance element may be connected in series with each of the conductive wires W1 to W8, and a voltage generated between the opposite terminals of the resistance element may be measured to allow the current to be calculated.

When the current is measured on a layer-by-layer basis as illustrated in FIG. 3A, the same voltage (for example, 5 V) is applied for each measurement using the DC power supply 11, to allow the current value to be measured. On the other hand, when the currents flowing through the layers L1 to L8 are simultaneously measured, as illustrated in FIG. 3B, a DC power supply 11$v$ that enables the applied voltage to be varied may be used to adjust the applied voltage for measurement so that the value of the current flowing throughout the specimen A remains unchanged even when the target specimen M is changed.

In any measurement methods, an electrode is formed on the front surface of an opposite end of the specimen M to a conductive wire connection side, and a common conductive wire Wc is connected to the electrode. A possible method for connecting the common conductive wire Wc may involve, for example, executing a sanding treatment on a part of the front surface of the specimen M, bringing the end of the conductive wire Wi into contact with the treated part, coating a conductive silver paste on the part, and heating and sintering the paste. Plating may be executed after the sanding treatment.

In the measurement method in FIG. 3B, by providing a Rogowski coil 12$t$ and an ammeter 13$t$, which allow the current flowing throughout the specimen M to be detected, the variable DC power supply 11$v$ may be controlled so that the current measured by the ammeter 13$t$ has a predetermined value.

Now, the results of current measurement for the specimen of the laminate composite material using the current measuring apparatus will be described.

FIG. 4A and FIG. 4B illustrate the structures of specimens used for measurement tests conducted by the inventors of the present invention. FIG. 4A illustrates a specimen A including eight CFRP layers L1 to L8 laminated together so that the carbon fibers in all the layers are arranged in the same direction. FIG. 4B illustrates a specimen B including eight CFRP layers L1 to L8 laminated together so that the carbon fibers in some of the layers are arranged in a direction different from the direction in which the carbon fibers in the other layers are arranged. In FIG. 4A and FIG. 4B, the layers illustrated with "0°" are layers in which the arrangement direction of the carbon fibers is the same as the longitudinal direction of the specimen, that is, the direction in which the current is to be passed. The layers illustrated with "90°" are layers in which the carbon fibers are arranged in a direction orthogonal to the longitudinal direction of the specimen, that is, a width direction of the specimen.

In other words, in the specimen A, the arrangement direction of the carbon fibers in all the layers L1 to L8 is the same as the direction in which the current is to be passed. On the other hand, in the specimen B, the carbon fibers in the layers L1, L3, L6, and L8 are arranged in the direction of the current, whereas the carbon fibers in the layers L2, L4, L5 and L7 are arranged in the direction orthogonal to the current direction. In FIG. 4B, the boundary between L1 and L2, the boundary between L3 and L4, the boundary between L5 and L6, and the boundary between L7 and L8 are illustrated by dashed lines. This is because prepregs used to produce the specimen B were obtained by laminating sheets with fibers arranged in directions of 0° and 90° and the specimen B was produced by appropriately shaping four prepregs laid on top of one another.

Figure 5:
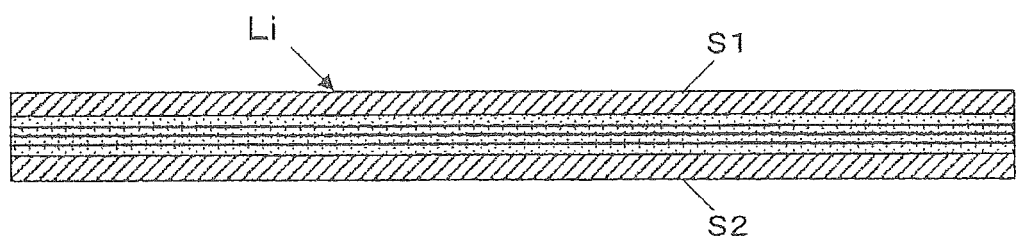
FIG. 5 is a diagram illustrating a cross-sectional structure of CFRP layers in a specimen produced for experiments.

As illustrated in FIG. 5, toughening layers S1 and S2 were formed on a front surface and a back surface, respectively, of each of the CFRP layers L1 to L8.

FIGS. 6A and 6B and FIGS. 7A and 7B illustrate the results of current measurement performed on the specimens A and B structured as described above using the measurement apparatus in FIG. 3B. The results of measurement are average values obtained when a given current was passed for a predetermined time.

Figure 6A:
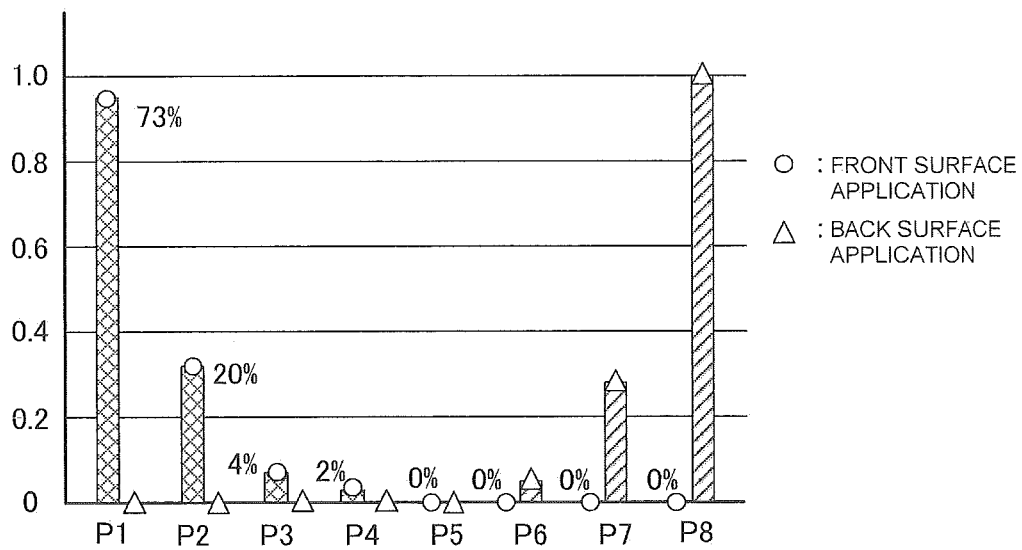
FIG. 6A and FIG. 6B are graphs illustrating the results of current measurement for the CFRP layers in the two specimens produced according to the first implementation.

FIG. 6A illustrates the results of measurement for the specimen A. FIG. GB illustrates the results of measurement for the specimen B. The axis of abscissas indicates the number of each layer, and the axis of ordinate indicates current ratio. The current value of the layer for which the largest current was measured was set to 1 so as to allow the relative magnitude (standardized current) of the current in each layer to be indicated. For both specimens A and B, the total current was 2 A. In this regard, the applied voltage was about 3.8 V.

Furthermore, for the specimen A, the value is illustrated for each layer. However, for the specimen B, the illustrated values correspond to the total current for the first and second layers, the total current for the third and fourth layers, the total current for the fifth and sixth layers, and the total current for the seventh and eighth layers. This is because the prepregs used to produce the specimen B were obtained by laminating sheets with fibers arranged in directions of 0° and 90° and the specimen B was produced by appropriately shaping four prepregs laid on top of one another. For such a specimen, preferably, the clip in FIG. 2A is used to connect the conductive wire, or the end of the conductive wire is connected, using the method in FIG. 2B, to the front and back of each of the (four) laminates resulting from separation.

Circles (meshed bars) indicate measured values obtained when a current was passed with the common conductive wire Wc connected to the P1 layer-side front surface. Triangles (hatched bars) indicate measured values obtained when a current was passed with the common conductive wire Wc connected to the P8 layer-side front surface (the back surface of the specimen). Furthermore, a percentage notation added to each mark is a value indicative of the ratio of the current flowing through each layer to the current flowing throughout the specimen.

Figure 6B:
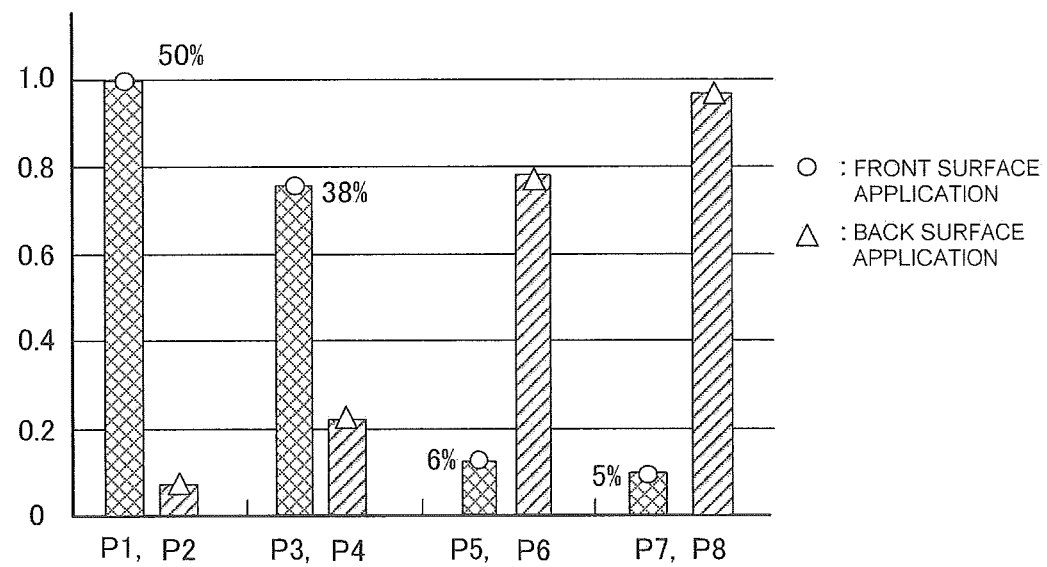

FIGS. 6A and 6B indicates that as shown in FIG. 5 even a composite material with CFRP layers laminated together and each including toughening layers on the front and back surfaces thereof allows currents to flow through the internal layers. Furthermore, a comparison between the results of measurement in FIG. 6A and the results of measurement in FIG. 6B clearly indicates that the specimens A and B are different from each other in the magnitude of the current flowing through each layer, that is, in current distribution.

Figure 7A:
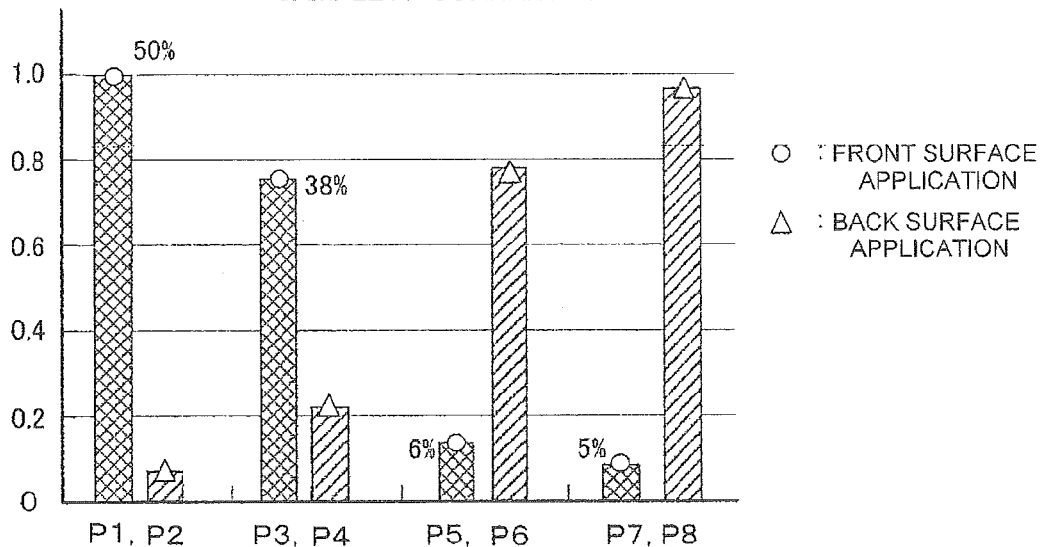
FIG. 7A and FIG. 7B are graphs illustrating the results of current measurement for CFRP layers in a specimen B which results are obtained when the value of a current passed through the specimen B is varied.
Figure 7B:
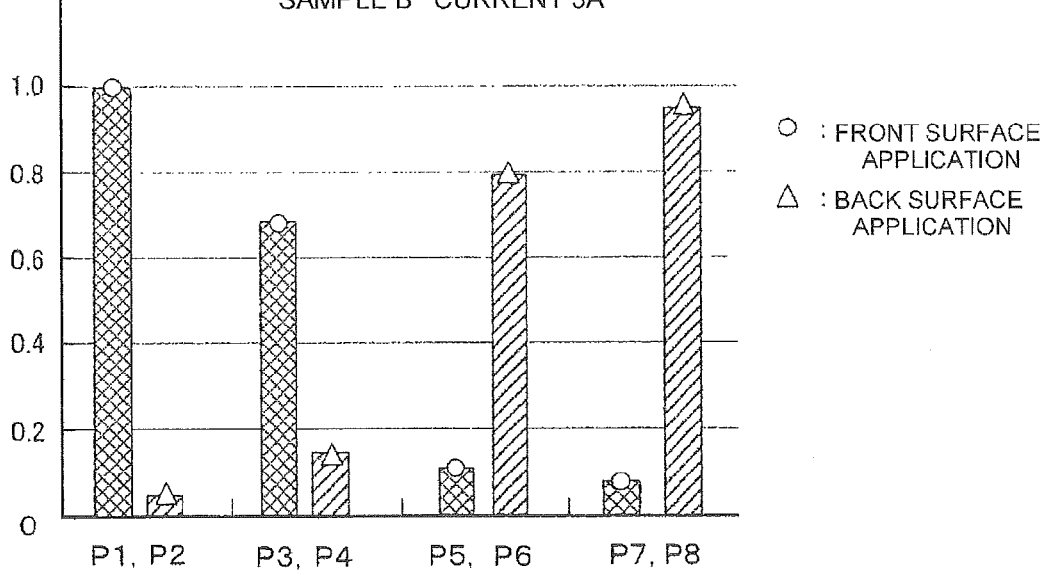

FIG. 7A illustrates the results of measurement (the same as the results in FIG. 6B) obtained when a current of 2 A was passed through the specimen B. FIG. 7B illustrates the results of measurement obtained when a current of 3 A was passed through the specimen B. The voltage applied when the current of 3 A was passed is about 5.9 V. The axis of abscissas indicates the number of each layer, and the axis of ordinate indicates the current value. Furthermore, as is the case with FIG. 6B, the illustrated values correspond to the total current for the first and second layers, the total current for the third and fourth layers, the total current for the fifth and sixth layers, and the total current for the seventh and eighth layers.

Meshed bars indicate measured values obtained when a current was passed with the common conductive wire Wc connected to the first layer P1-side front surface. Hatched bars indicate measured values obtained when a current was passed with the common conductive wire Wc connected to the eighth layer P8-side front surface (the back surface of the specimen).

A comparison between the results of measurement in FIG. 7A and the results of measurement in FIG. 7B indicates that no significant difference is observed in the distribution of currents among the layers even with a change in the current flowing throughout the specimen.

The conventional current measuring method fails to determine the ratios of currents flowing through the respective layers in the laminate composite material (the current distribution in the thickness direction of the material). However, the use of the current measuring method according to the first implementation allows the ratios of currents flowing through the respective layers to be determined.

Thus, the results of current measurement allow estimation of the distribution of currents flowing through the composite material to be used when a lightning stroke occurs.

For example, for airplanes, it may be desirable to pass a larger current in the vicinity of the front surface of the material or reduce the current density in a layer close to the front surface, depending on an area in which the material is used. In such a case, the current measuring method according to the first implementation allows materials with fibers arranged in different directions to be appropriately used.

Furthermore, if the composite material to be used has already been determined in terms of strength and the like, when the material is determined to be characterized in that a larger current flows in the vicinity of the front surface of the material, for example, a measure to join a metallic plate to the front surface to reduce the current density in the surface layer can be taken.

In actual airplanes, a metallic component referred to as a fastener may be used to couple composite materials together. In such a case, currents concentrate on a part of the fastener during a lightning stroke. Thus, the distribution of currents flowing in the presence of the fastener may desirably be determined.

Figure 8:
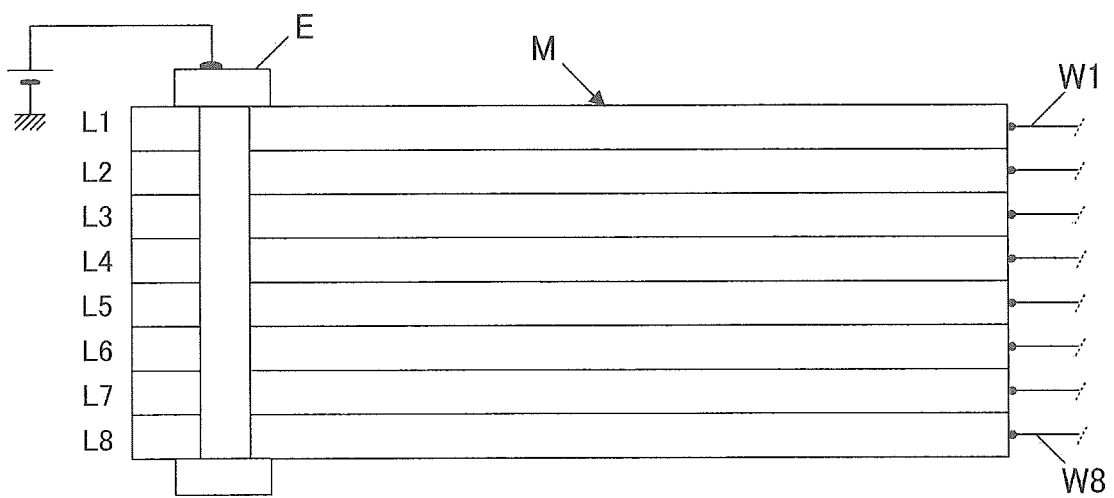
FIG. 8 is a diagram illustrating another example of connection of a common conductive wire to a specimen.

Thus, for example, an electrode E may be provided which is a conductive element penetrating all the CFRP layers L1 to L8, and a current may be applied to the electrode E, with a current flowing through each layer measured, as illustrated in FIG. 8.

Figure 9:
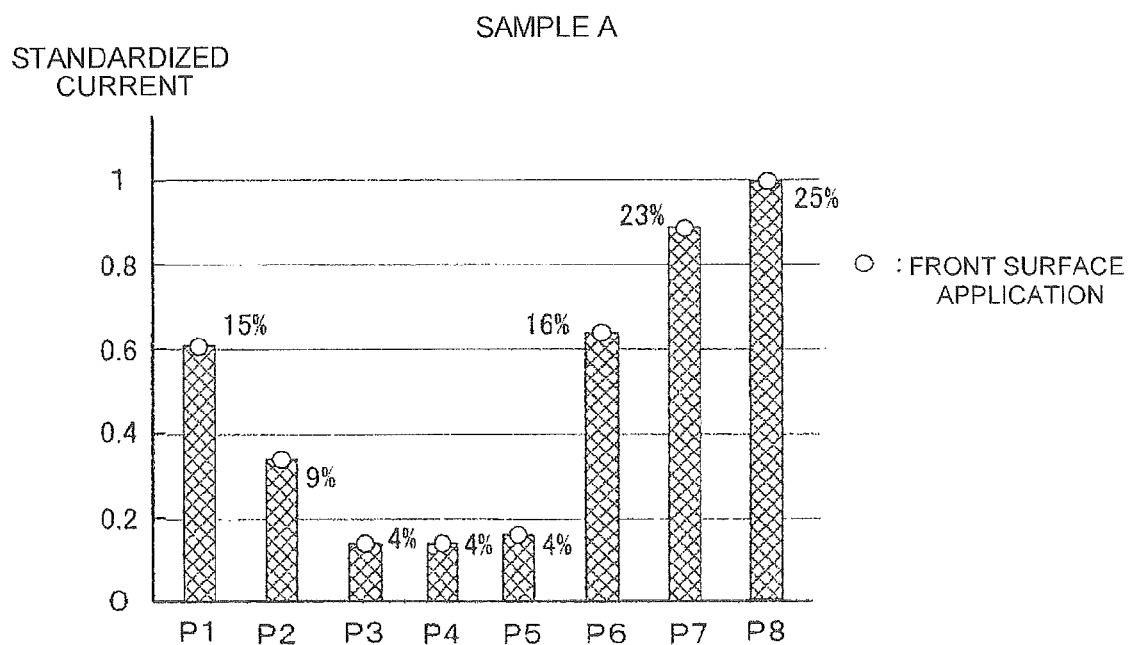
FIG. 9 is a graph illustrating the results of current measurement for CFRP layers in the specimen including electrodes, as illustrated in FIG. 8.

FIG. 9 illustrates the results of current measurement for a specimen A (in which all the eight layers have a fiber arrangement direction of 0°) including, as the electrode E illustrated in FIG. 8, a bolt which penetrates the layers and which includes a nut screwed around a tip of the bolt. The serial numbers for the layers are on the x-axis while relative magnitudes (normalized currents) of currents of the layers are on the y-axis. 3 A signifies a total current. The level of voltage applied at this time is about 3.3 V.

A comparison between the results of measurement in FIG. 9 and the results of measurement in FIG. 6A indicates that the application of a current through the electrode E increases the currents flowing through the P2 to P8 layers. The comparison also indicates that, even though a current is passed through the front surface side of the P1 layer, the currents flowing through the P6 to P8 layers are larger not only than the currents flowing through the P3 to P5 layers but also than the currents flowing through the P1 to P3 layers. The cause is expected to be due to a difference in the manner of the contact between the end of the electrode (the head of the bolt or the nut) and the front surface of the specimen, a difference in the manner of generation of burrs during drilling, a difference in the manner of sanding, and the like.

Figure 10:
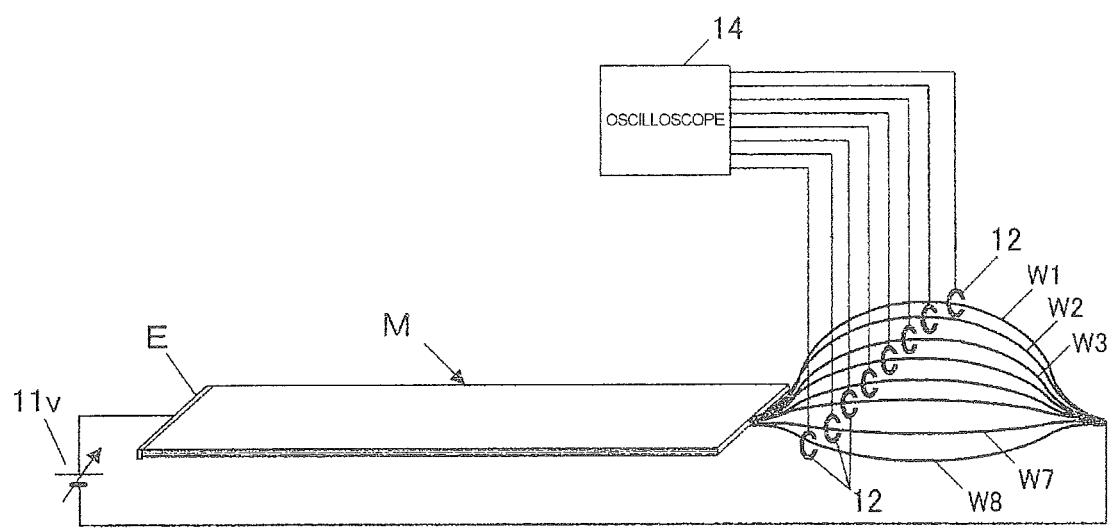
FIG. 10 is a diagram illustrating a current measuring method for CFRP layers in a specimen with electrodes on end surfaces thereof.
Figure 11:
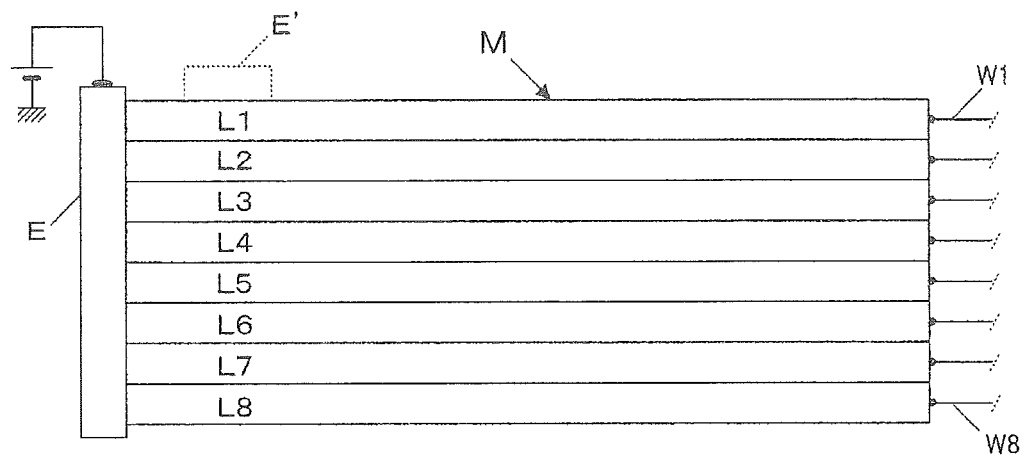
FIG. 11 is a diagram illustrating an example of connection of the common conductive wire to the specimen according to the current measuring method illustrated in FIG. 10.

Furthermore, the inventors attached the electrode E to an end surface of the specimen M opposite to a layer release side and conducted experiments in which a current was applied to the electrode E, with a current flowing through each layer measured, as illustrated in FIG. 10. The measurement target specimen was the specimen A in which all the eight layers had a fiber arrangement direction of 0°, and the total current was 3 A. In this regard, the applied voltage was about 0.7 V. FIG. 11 is a diagram illustrating an example of connection of the common conductive wire to the specimen according to the current measuring method illustrated in FIG. 10. FIG. 12 illustrates the results of current measurement.

FIG. 12 indicates that an approximately uniform current flows through the P1 to P8 layers. This result is substantially as expected, and the current measuring apparatus is assumed to pose no problem.

In FIG. 11, an example of an electrode that applies a current to the specimen M though the front surface thereof is illustrated by a dashed line E'.

The implementation to which the present invention is applicable is not limited to the first implementation, which may be appropriately varied without departing from the spirits of the present invention.

For example, in one of the specimens M described above in the first implementation, all the layers have the same fiber arrangement direction, whereas, in the other specimen M, some of the layers have a fiber arrangement direction different from the fiber arrangement direction in the other layers by 90°. However, the specimens M are not limited to these examples. The specimen may include four different types of layers laminated together and having respective fiber arrangement directions that are different from one another by 45°. Furthermore, the number of layers laminated together is not limited to eight. Moreover, a specimen with a fastener provided in the middle thereof may be produced so as to allow measurement of the distribution of currents flowing through the respective layers in the presence of the fastener. In this case, the fastener may be utilized as an electrode (conductive element) that allows a current to be applied.

Furthermore, in the first implementation of the present invention, the common conductive wire and the discrete conductive wires (W1 to W8) are connected to the respective opposite ends of the specimen M. However, the present invention is not limited to this configuration. For example, the common conductive wire may be connected to the center of the specimen M, or the CFRP layers may be exposed at a plurality of ends of the specimen M, with the discrete conductive wires connected to each of the ends.

Additionally, in the first implementation, the release films are used to allow the CFRP layers to be released. However, the present invention is not limited to this configuration. The CFRP layers may be released using a jig after the specimen M is appropriately shaped.

(Second Implementation)

Figure 13A:
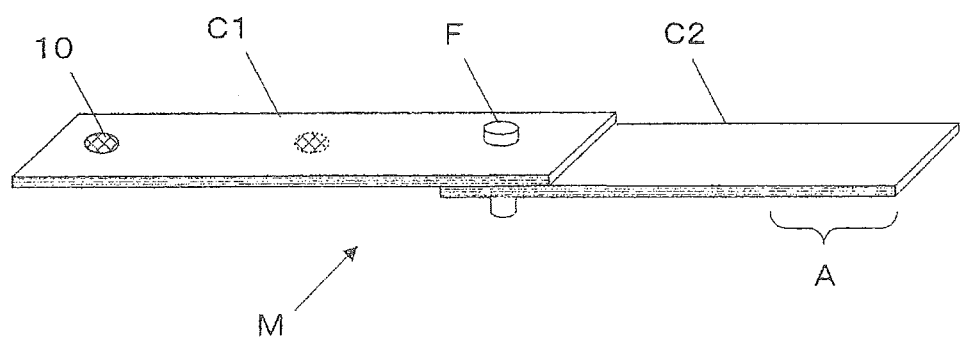
FIG. 13A and FIG. 13B are diagrams illustrating a specimen (test piece) using a laminate composite material to which a current measuring method according to a second implementation is applied and the current measuring method.
Figure 13B:
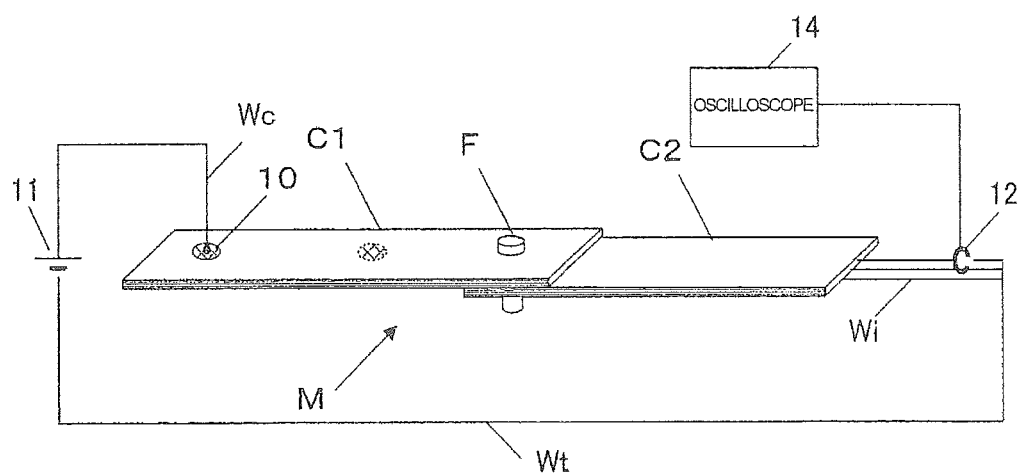

FIG. 13A and FIG. 13B illustrate a specimen (test piece) which includes a laminate composite material and to which a current measuring method according to a second implementation is applied, and the current measuring method.

As illustrated in FIG. 13A, a specimen M according to the second implementation includes two composite material plates C1 and C2 laid on top of each other at ends thereof and coupled together using a metallic fastener F. The composite material plate C1 includes an electrode 10 formed on a front surface of an opposite end (in FIGS. 13A and 13B, a left end) to a coupling side and serving as a current applier. At an end (in FIGS. 13A and 13B, a right end) of the composite material plate C2 opposite to the coupling side, as explanation will be provided later the layers in the composite material plate C2 are separated from one another over a range equal to a predetermined length A. Composite materials constituting the composite material plates C1 and C2 are fiber reinforced plastic including a resin reinforced with conductive fibers. In the second implementation, these composite materials are carbon fiber reinforced plastic (CFRP) containing carbon fibers. Each of the composite materials is shaped like a strip.

The specimen M according to the second implementation allows a positive current to be applied by a DC power supply 11 via a conductive wire Wc to an electrode 10 on a front surface of an end of the composite material sheet C1, as illustrated in FIG. 13B. Furthermore, ends of layers in the composite material sheet C2 are connected to a negative electrode of the DC power supply 11 using conductive wire Wi and Wt. A current flowing through the conductive wire Wi is detected by a current detection element 12 so that the detected current value is displayed by an oscilloscope 14. The DC power supply 11, the current detection element 12, and the oscilloscope 14 provide a current measuring apparatus.

A possible manner of forming the electrode 10 involves, for example, executing a sanding treatment on a part of the front surface of the composite material sheet C1, bringing an end of the conductive wire Wc into contact with the treated part, coating a conductive silver paste on the part, and heating and sintering the paste. Plating may be executed after the sanding treatment.

The composite material plates C1 and C2 providing the specimen M are each a laminated composite material formed by laminating a plurality of prepregs serving as the composite material sheets of the present invention and each including a plurality of carbon fiber bundles arranged along a predetermined direction and impregnated with an uncured resin.

Figure 14:
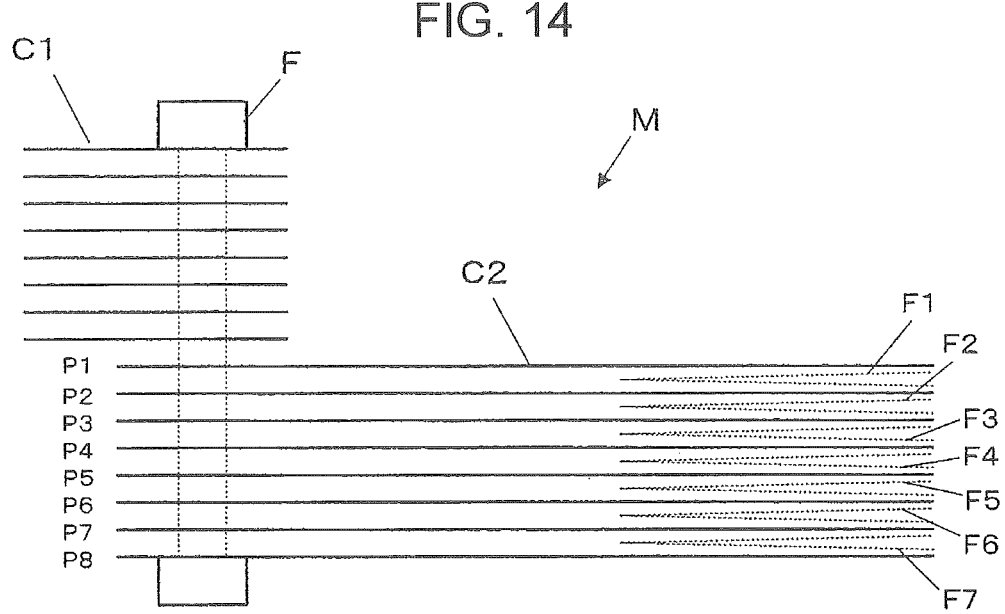
FIG. 14 is a diagram illustrating how to configure composite material plates providing the specimen (test piece) according to the second implementation illustrated in FIGS. 13A and 13B.

In the second implementation, the composite material plate C2 is obtained by laminating eight prepregs P1 to P8 together and appropriately shaping the laminated prepregs P1 to P8 as illustrated in FIG. 14. Each of the prepregs P1 to P8 is 1 mm or less (for example, 0.2 mm) in thickness. Additionally, the carbon fibers in each of the layers in the prepregs P1 to P8 are arranged in any direction. The direction is selected so as to correspond to the structure of an actual composite material considered to be used for airplanes and the like. The number of prepregs laminated together is optionally selected so as to correspond to the structure of the actual composite material. The composite material plates C1 and C2 may be different from each other in thickness.

Moreover, the composite material plate C2 in the specimen M according to the second implementation includes spacing elements each disposed between the prepreg layers and extending from an end of the composite material plate C2 opposite to a coupling side with a fastener F toward the center of the composite material plate C2. Specifically, as illustrated in FIG. 14, films (hereinafter referred to as release films) F1 to F7 with the opposite surfaces thereof subjected to a release facilitating treatment are each interposed between the layers so as to extend over a predetermined length from one end (in FIG. 14, a right end) to the middle of the composite material plate C2 in a longitudinal direction. Furthermore, in the second implementation, each of the release films F1 to F7 is folded in the middle before being inserted between the layers. This structure is used to prevent a situation where, when the release film is a single film that is not folded in the middle, the film may stick to the surfaces of the prepregs to make separation of the adjacent prepreg layers difficult when the release facilitating treatment is uneven. However, the release film is not limited to the folded film that is folded in the middle but may be a single film that is not folded in the middle. The release facilitating treatment for the layers is not executed on the composite material plate C1.

A material for the release film may desirably be a heat-resistant insulating material, for example, Kapton (registered trademark), a type of polyimide rein. The release facilitating treatment executed on the surface of the release film involves, for example, coating of Frekote (registered trademark) as a release agent. The coated release agent is not limited to Frekote but may be any heat-resistant insulating material. The spacing element is not limited to the release film but may be an insulating material such as a silicone rubber sheet or a metallic sheet or the like with a release agent coated thereon. Furthermore, the spacing element is not limited to the thin sheet-like element but may be a wedge- or plate-like resin or a metallic jig with a release agent coated on the surface thereof.

As described above, the CFRP composite material plate C2 constituting the specimen M is manufactured by heating, under pressure, the laminated prepregs P1 to P8 with the spacing elements such as the release films each interposed between the prepreg layers at one end thereof to cure the resin. Subsequently, the specimen M is completed by connecting a conductive wire through which a measurement current flows to a release side end of each of the CFRP layers, forming a through-hole at the coupling-side end by drilling or the like, and coupling the composite material plates C1 and C2 using the fastener F. In the second implementation, after the specimen is complete, the release films are released for tests. However, the release films may remain interposed between the layers. When used as the spacing elements, metallic sheets are preferably removed after the specimen is complete.

When the spacing elements are removed, insulating elements are preferably inserted between the layers in order to ensure insulation between the layers during measurement.

A method for manufacturing a specimen is not limited to the method of laminating a plurality of prepregs together and curing the resin as described above. Another method such as an RTM method may be used for manufacturing. For example, a VaRTM method, a type of the RTM method, is a shaping method of arranging a plurality of carbon fiber bundles along a predetermined direction, wrapping the entire carbon fiber bundles with a bag film, vacuumizing the wrapped carbon fiber bundles, injecting a liquid resin into the carbon fiber bundles to impregnate the fibers with the resin, and then using an oven to heat the carbon fiber bundles impregnated with the resin to cure the resin. To manufacture a specimen with the above-described structure using the VaRTM method, the following procedure may be taken. A plurality of carbon fiber bundles is arranged along a predetermined direction. Spacing elements such as a plurality of release films are interposed among the carbon fiber bundles on one side thereof at predetermined intervals. The carbon fiber bundles are entirely wrapped with a bag film. The wrapped carbon fiber bundles are vacuumized. A liquid resin is injected into the vacuumized carbon fiber bundles.

Furthermore, the method for manufacturing a specimen may be a technique based on cold curing such as wet layup. In this case, the spacing elements need not offer heat resistance, and thus any of a wide variety of spacing elements may be selected for this purpose.

Figure 15A:
FIG. 15A and FIG. 15B are each a diagram illustrating an example of connection of conductive wires to respective CFRP layers in the specimen.
Figure 15B:
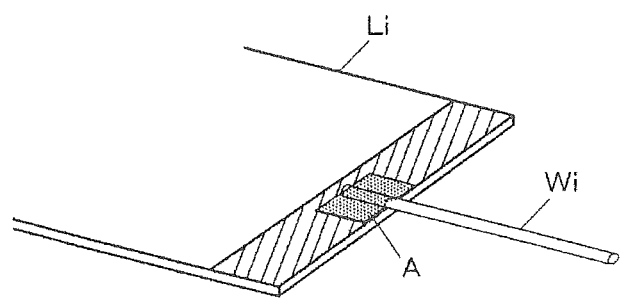

FIGS. 15A and 15B illustrate an example of connection of a conductive wire Wi to each CFRP layer (composite material sheet) in the composite material plate C2. Before the conductive wire is connected, a sanding treatment is executed on the end of each CFRP layer Li so that the resin at the end of each CFRP layer Li is, for example, filed off to expose the carbon fibers. Furthermore, the area subjected to the sanding treatment is preferably further plated. The plating is preferably two-step plating. Moreover, before the plating, the area is preferably pre-treated by applying a treatment liquid such as sulfuric acid to the area. To expose the carbon fibers, any measure other than the sanding treatment may be used such as dissolution and decomposition of the resin using a chemical.

FIG. 15A illustrates that a clip electrode (terminal) Ti is connected to an end of the CFRP layer Li and that the conductive wire Wi is connected to the electrode Ti by soldering or the like. FIG. 15B illustrates that the conductive wire Wi is connected directly to the end of the CFRP layer Li by bringing an end of the conductive wire Wi into contact with the end of the CFRP layer Li, coating a conductive silver paste A on the conductive wire, and heating and sintering the silver paste A. A hatched area in FIG. 15B is the area subjected to the sanding treatment.

Now, a current measuring method using the specimen of the above-described laminate composite material will be described.

Figure 16A:
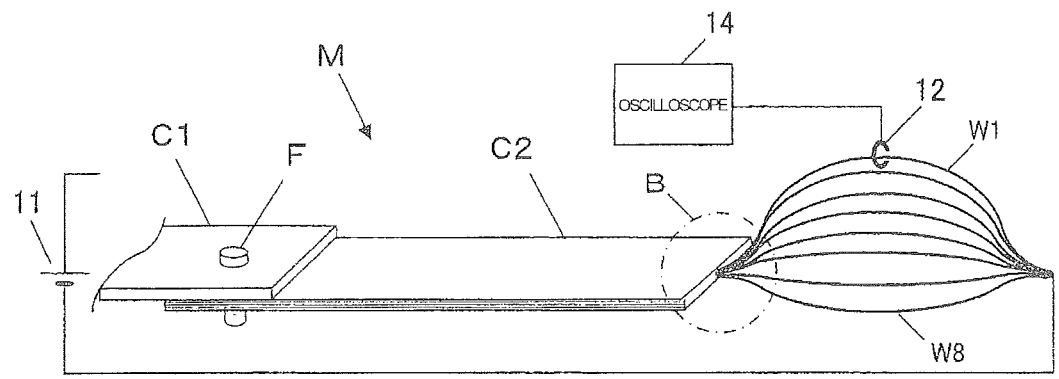
FIG. 16A and FIG. 16B are each a diagram illustrating a method for measuring a current flowing through each of the CFRP layers in the specimen.
Figure 16B:
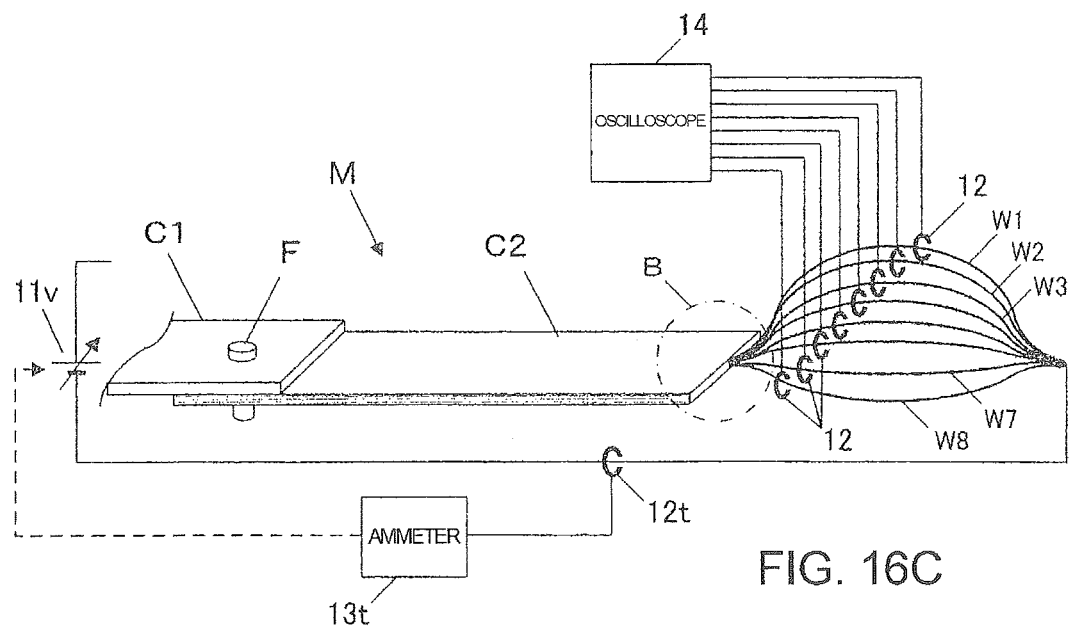
Figure 16C:
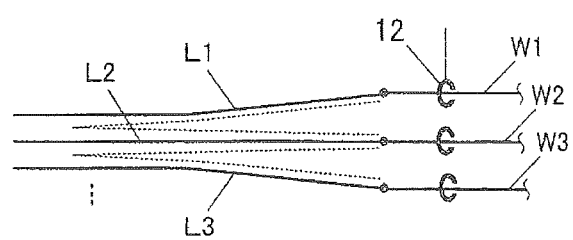
FIG. 16C is an enlarged diagram of a part of FIG. 16A and FIG. 16B which is enclosed by an alternate long and short dash line.

FIGS. 16A to 16C schematically illustrates a current measuring apparatus and the current measurement method both intended for the specimen M. As illustrated in FIGS. 16A and 16B, the current measuring apparatus includes a DC power supply 11, a Rogowski coil 12 that allows detection of a current flowing through the conductive wire Wi connected to the end of each CFRP layer Li in the specimen, and an oscilloscope 14 connected to the Rogowski coil 12. To check how a current flows when a current waveform (for example, a waveform conforming with the standard specification SAE ARP 5412 for a lightening waveform for airplanes) similar to a lightning current is applied to the specimen, the Rogowski coil 12 corresponding to the frequency band of the lightning waveform may be connected to the oscilloscope 14.

FIG. 16A illustrates that a current flowing through the CFRP layer Li in the specimen is measured on a layer-by-layer basis. Currents are sequentially measured, with a conductive wire, on which the Rogowski coil 12 is disposed, being selected. FIG. 16B illustrates that currents flowing through all the CFRP layers L1 to L8 in the specimen M can be simultaneously measured. The Rogowski coil 12 is disposed on each of the conductive wires W1 to W8. FIG. 16C is an enlarged diagram of a part of FIG. 16A and FIG. 16B which is enclosed by an alternate long and short dash line B. The conductive wires W1, W2, W3, . . . , are connected to the ends of the respective CFRP layers L1, L2, L3, . . . which are separated from one another.

The Rogowski coil is an annular coil that enables a large current to be measured, and when disposed to surround a measurement point, enables the current to be measured based on voltages induced at the opposite ends of the coil. The current detection element is not limited to the Rogowski coil but may be any other current sensor. Alternatively, a resistance element may be connected in series with each of the conductive wires W1 to W8, and a voltage generated between the opposite terminals of the resistance element may be measured to allow the current to be calculated.

When the current is measured on a layer-by-layer basis as illustrated in FIG. 16A, the same voltage (for example, 5 V) is applied for each measurement using the DC power supply 11, to allow the current value to be measured. On the other hand, as illustrated in FIG. 16B, when the currents flowing through the layers L1 to L8 are simultaneously measured, a DC power supply 11v that enables the applied voltage to be varied may be used to adjust the applied voltage for measurement so that the value of the current flowing throughout the specimen M remains unchanged even when the target specimen M is changed.

Even when the current is measured on a layer-by-layer basis as illustrated in FIG. 16A, as illustrated in FIG. 16B a Rogowski coil 12t and an ammeter 13t which allow the current flowing throughout the specimen M to be detected may be provided and the DC power supply 11v capable of changing application voltage may be used. The voltage of the variable DC power supply 11v may be controlled so that the current measured by the ammeter 13t has a predetermined value.

The inventors conducted tests in which the currents in the specimen of the above-described laminate composite material were measured using the current measuring apparatus configured as described above. The results of the tests will be described below.

Figure 17:
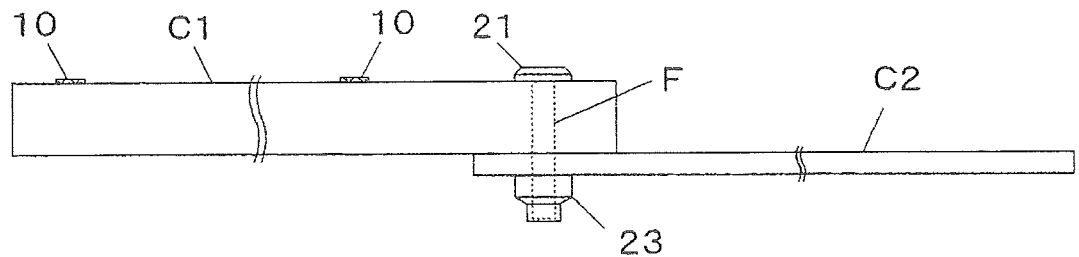
FIG. 17 is a diagram illustrating a specific configuration of a specimen produced for experiments conducted to verify the effects of the second implementation.

FIG. 17 illustrates a specific example of the structure of a specimen used for the measurement tests. FIGS. 18A and 18B illustrate a specific example of a bolt used to couple the two composite material plates C1 and C2 together. The two composite material plates C1 and C2 providing the specimen illustrated in FIG. 17 are 390 mm and 250 mm, respectively, in length, and are both 50 mm in width. The thickness of the composite material plate is 9 mm for C1 and 2 mm for C2. An overlapping area between the composite material plates C1 and C2 is 50 mm in length. A through-hole for a fastener was formed in each of the composite material plates C1 and C2 so that the center of the through-hole was disposed 25 mm away from the corresponding ends of the composite material plates C1 and C2. The electrodes 10 were formed at positions 50 mm and 250 mm, respectively, away from the through-hole. The fastener F was a bolt with a diameter of 5 mm.

In the specimen M used for the measurement tests, the composite material plate C1 is thicker than the composite material plate C2, as illustrated in FIG. 17. This is because a commercially available bolt with a predetermined length was used as the fastener F. That is, no commercially available fastener has an extremely short bolt, while the time needed to produce the specimen increases when the number of composite material plates C2 laminated together is increased in accordance with the length of the bolt. Thus, the thickness of the composite material plate C1 was adjusted in accordance with the length of the bolt. Specifically, the composite material plate C2 produced according to the second implementation and including eight CFRP layers was 2 mm in thickness, and the available bolt was 11 mm in length. Consequently, the thickness of the composite material plate C1 was set to 9 mm.

The fastener F used is what is called a sleeve fastener including a sleeve 22 with an inner diameter slightly smaller than the outer diameter of a straight area of the bolt 21, as illustrated in FIG. 18A. The sleeve 22 of the sleeve fastener is fitted into the through-holes in the composite material plates C1 and C2. Then, the bolt 21 is inserted into the sleeve 22. A nut 23 with an internal thread is fitted, in a threaded manner, over an external thread at a tip of the bolt projecting from the bottom of the sleeve, and screwed. Then, the bolt 21 moves toward the nut while deforming the sleeve 22 (increasing the diameter of the sleeve 22). This reduces the gap between the bolt 21 and the inner peripheral surface of the machined holes (through-hole) formed in the composite material, resulting in a coupling state with an appropriate contact, as illustrated in FIG. 18B.

Figure 20:
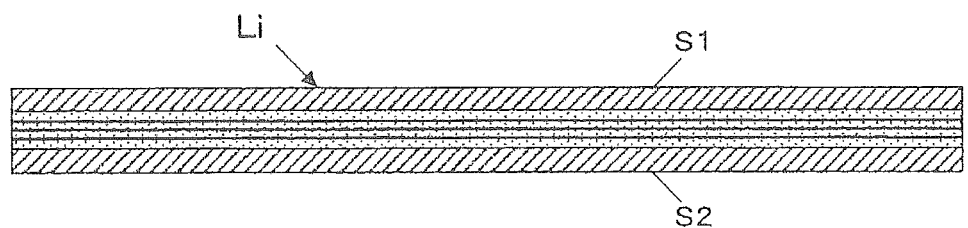
FIG. 20 is a diagram illustrating a cross-sectional structure of CFRP layers in a specimen produced for experiments.

FIG. 19A illustrates the structure of the composite material plate C2 providing the specimen used for the measurement tests conducted by the inventors. The specimen includes eight CFRP layers L1 to L8 laminated together, with the carbon fibers in all the layers being arranged in the same direction. As illustrated in FIG. 20, toughening layers S1 and S2 were formed on a front surface and a back surface, respectively, of each of the CFRP layers L1 to L8. Measurement may also be performed, using the above-described current measuring apparatus, on a composite material plate including eight CFRP layers L1 to L8 laminated together, with the carbon fibers in some of the layers being arranged in a direction different from the direction in which the carbon fibers in the other layers are arranged, as illustrated in FIG. 19B. In FIG. 19A and FIG. 19B, the layers illustrated with "0°" are layers in which the arrangement direction of the carbon fibers is the same as the longitudinal direction of the specimen, that is, the direction in which the current is to be passed. The layers illustrated with "90°" are layers in which the carbon fibers are arranged in a direction orthogonal to the longitudinal direction of the specimen, that is, a width direction of the specimen.

In other words, in FIG. 19A, the arrangement direction of the carbon fibers in all the layers L1 to L8 is the same as the direction in which the current is to be passed. On the other hand, in FIG. 19B, the carbon fibers in the layers L1, L3, L6, and L8 are arranged in the direction of the current, whereas the carbon fibers in the layers L2, L4, L5, and L7 are arranged in the direction orthogonal to the current direction. In FIG. 19B, the boundary between L1 and L2, the boundary between L3 and L4, the boundary between L5 and L6, and the boundary between L7 and L8 are illustrated by dashed lines. This is due to the assumption that prepregs used to produce the composite material plates are obtained by laminating sheets with fibers arranged in directions of 0° and 90°.

FIGS. 21A to 21C and FIGS. 22A to 22C illustrate the results of current measurement performed, using the measurement apparatus in FIG. 16B, on three specimens #1, #2, and #3 having such a structure as shown in FIG. 17 and using the bolt in FIGS. 18A and 18B as a fastener; the results are illustrated for each of the layers in the specimens. In the graphs in FIGS. 21A to 21C and FIGS. 22A to 22C, the axis of abscissas indicates the number of each layer, and the axis of ordinate indicates the current value. The results of measurement are average values obtained when a given current (2.4 A in total) was passed for a predetermined time.

FIG. 21A is a graph representing the current values for the layers L1 to L8 measured when a voltage was applied to the electrode disposed away from the position of the fastener in each of the specimens #1, #2, and #3. FIG. 21B is a graph representing the ratio of the current value for each layer to the total current value in percentage (%).

FIG. 21A and FIG. 21B illustrate that an approximately uniform current flows through the layers L1 to L8. This indicates that, when the sleeve as illustrated in FIGS. 18A and 18B is used as a fastener, the inner peripheral surface of the machined hole (through-hole) and the bolt are in appropriate contact.

Furthermore, FIG. 22A, FIG. 22B, and FIG. 22C are graphs representing the current values for the layers L1 to L8 measured when, in each of the specimens #1, #2, and #3, voltages are applied to the electrodes disposed away from and close to the position of the fastener, respectively, and the ratios of the current values. In FIG. 22A, FIG. 22B, and FIG. 22C, meshed bars indicate the current values for the layers L1 to L8 measured when a voltage was applied to the electrode disposed close to the position of the fastener. Hatched bars indicate the current values for the layers L1 to L8 measured when a voltage was applied to the electrode disposed away from the position of the fastener.

FIGS. 22A to 22C indicate that there is no significant difference in current value and ratio among the layers both when the voltage is applied to the electrode disposed away from the position of the fastener and when the voltage is applied to the electrode disposed close to the position of the fastener.

Figure 23:
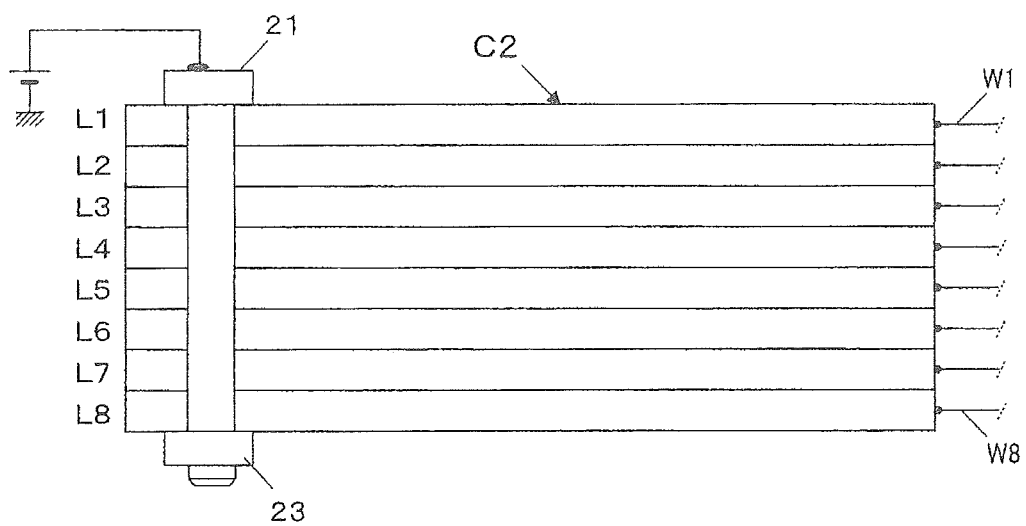
FIG. 23 is a diagram illustrating an example in which a fastener with no sleeve is allowed to penetrate composite material plates providing a specimen and in which a common conductive wire is connected to the fastener.
Figure 24:
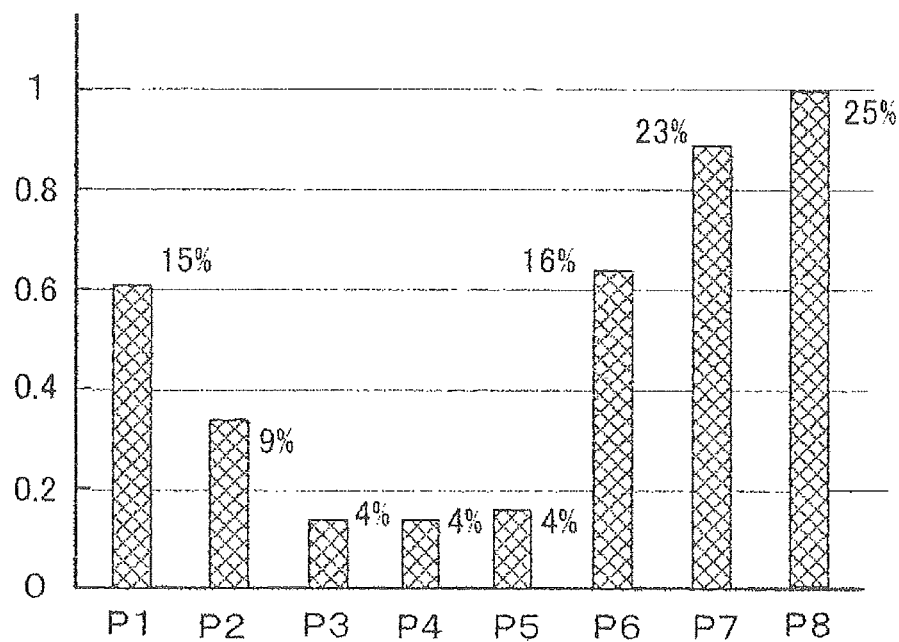
FIG. 24 is a graph illustrating the results of current measurement for CFRP layers in composite material plates with a fastener as illustrated in FIG. 23.

On the other hand, the inventors conducted tests as follows. As illustrated in FIG. 23 a composite material plate similar to the composite material plate C2 in the specimen according to the second implementation was prepared as a measurement target. The bolt 21 with no sleeve was allowed to penetrate an end of the plate opposite to the layer spacing side, with the nut 23 fitted over the tip of the bolt 21 in a threaded manner. A voltage was applied to the bolt 21, serving as an electrode, and the resultant current was measured. FIG. 24 illustrates the results of the current measurement. The axis of abscissas indicates the number of each layer, and the axis of ordinate indicates the relative magnitude (standardized current) of the current in each layer. The total current was 3 A. In this regard, the applied voltage was about 3.3 V. Based on the results of the measurement in FIGS. 21A and 21B and FIGS. 22A to 22C, the results of the measurement in FIG. 24 are expected to be approximately equal to the results of current measurement obtained when a bolt with no sleeve is used as the fastener F in the specimen M illustrated in FIG. 17 (the specimen formed by coupling two composite material plates together).

A comparison between the results of measurement in FIG. 24 and the results of measurement in FIG. 21B indicates that, when the bolt with no sleeve was used as the fastener F, the currents flowing through the P6 to P8 layers are larger not only than the currents flowing through the P3 to P5 layers but also than the currents flowing through the P1 to P3 layers. In other words, a variation in current among the P1 to P8 layers is more significant when the bolt with no sleeve is used than when the bolt with the sleeve is used. As described above, the cause of the currents flowing through the P6 to P8 layers being larger not only than the currents in the P3 to P5 layers but also than the currents in the P1 to P3 layers is expected to be a difference in the manner of the contact between the end of the electrode (the head of the bolt or the nut) and the front surface of the specimen, a difference in the manner of generation of burrs during drilling, and the like.

The second implementation allows measurement of the currents flowing through the layers in the composite material plates providing the specimen and coupled together using the fastener to determine the ratios of the currents and the like. Thus, current measurement can be performed on a plurality of specimens with varying fasteners and varying machining conditions so that, based on the results of the measurement, a clue can be found about clarification of a current propagation mechanism also regarding an out-of-plane direction in a structure of a plurality of laminate composite materials coupled together using a fastener. Furthermore, the second implementation allows determination of the form and size of a fastener, machining conditions for the fastener, a laminate configuration of composite materials, and the like all of which are effective for lightning protection measures. The "machining conditions" as used herein include the type of a tool such as a drill which is used for drilling, and parameters such as rotation speed and feed speed.

(Variation)

Figure 25:
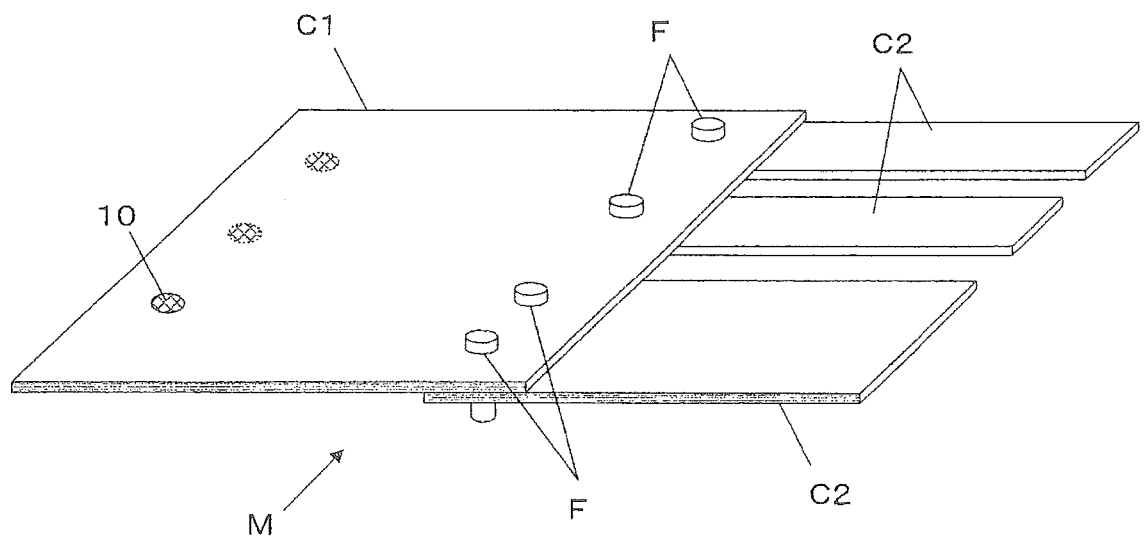
FIG. 25 is a perspective view illustrating a variation of the specimen according to the second implementation illustrated in FIGS. 13A and 13B.

FIG. 25 illustrates a variation of the specimen according to the implementation.

When a fuselage of an airplane is configured using composite materials, a plurality of composite materials are coupled together using fasteners inserted though respective plurality of through-holes formed in the composite materials at predetermined intervals (for example, 40 mm to 50 mm).

In view of such actual use conditions, the specimen according to the variation allows currents to be measured to determine how the currents flow when two composite material plates are coupled together using a plurality of fasteners.

In a specimen M illustrated in FIG. 25, a composite material plate C1 with an electrode formed thereon is large in width and has a plurality of through-holes formed along an end of the composite material plate C1 opposite to the electrode 10 and through which fasteners F are inserted. The composite material plate C1 thus allows a plurality of composite material plates C2 to be coupled thereto. At an end (in FIG. 25, a right end) of each of the composite material plates C2, the layers are separated from one another using release films or the like, as is the case with the composite material plates described above in the implementations.

FIG. 25 illustrates that three composite material plates C2 are co upled to one composite material plate C1 and that one of the composite material plates C2 is coupled to the composite material plate C1 using two fasteners F. However, one composite material plate C1 may be coupled to each of the composite material plates C2 for current measurement. Furthermore, as illustrated in FIG. 25, a current may be simultaneously passed through all three composite material plates C2 coupled to the composite material plate C1, with a current flowing through each layer in each plate measured.

Moreover, with a voltage applied to the electrode 10 to pass a current toward the composite material plate C2, a tester bar may be brought into contact with each of the fasteners F to allow the measurement apparatus to detect a voltage, thus allowing measurement of the current distribution in the composite material plate C1 with the electrode formed thereon.

Furthermore, a plurality of electrodes E may be formed on the composite material plate C1 as illustrated by a dashed line in FIG. 25, and the electrode to which the voltage is applied may be selected, with a current flowing to each composite material plate C2 measured.

The implementation of the present invention has been explained as thus. However, the present invention is not limited to the implementation, which may be appropriately varied without departing from the spirits of the present invention.

For example, in the implementation, all the layers in the specimen M have the same fiber arrangement direction. However, the specimen M is not limited to this example. The specimen may include layers laminated together and having fiber arrangement directions that are different from one another by 90° or include four different types of layers laminated together and having respective fiber arrangement directions that are different from one another by 45°.

Furthermore, in the implementation of the present invention, the electrode 10 to which a common conductive wire is connected is formed on the front surface of the composite material plate C1 in the specimen M. However, the formation of the electrode 10 is not limited to the front surface of the composite material plate C1. For example, such an electrode pin (including a fastener) that penetrates the composite material plate C1 may be provided at the position of the surface electrode illustrated in FIGS. 13A and 13B. Alternatively, such a plate-like electrode that contacts the entire end surface of the composite material plate C1 opposite to the coupling side may be provided.

Additionally, in the implementation, the release films are used to allow the CFRP layers to be released. However, the present invention is not limited to this configuration. The CFRP layers may be released using a jig after the specimen M is appropriately shaped.

In addition, the implementation uses the flat plate-like composite material plates C1 and C2. However, the present invention is not limited to these composite material plates. The composite materials may be structures with complicated shapes.

Furthermore, in the implementation, the electrode 10 has been described as a current applier. However, the current applier is not limited to the electrode 10 but may be one on which no processing is implemented on a portion to which a current is applied in a broad sense, or in an extreme case, no processing is implemented on an untreated composite material plate C1. For example, when lightning tests are conducted, the current measurement according to the present invention can be achieved by applying a discharge current onto the composite material plate C1 with no electrode formed thereon.

The implementations and variations of the present invention allow measurement of the current flowing through each layer in the laminate composite material. This enables finding of a clue about clarification of a current propagation mechanism in, for example, an out-of-plane direction and also enables determination of an effective lightning resistance measure and addressing short-circuit effectively.

Furthermore, the implementations and variations of the present invention allow measurement of the current flowing through each layer in the plurality of laminate composite materials coupled together by the fastener. This enables finding of a clue about clarification of the current propagation mechanism, for example, in an out-of-plane direction in the structure of the plurality of laminate composite materials coupled together by the fastener and also enables determination of the configuration and size of the fastener, machining conditions for the fastener, and the like, all of which are effective for preventing possible discharge from the fastener.

The invention claimed is:

1. A specimen comprising:
multiple composite material sheets that are laminated together and include conductive fibers,
wherein spacing elements that space the composite material sheets from one another are provided between the composite material sheets at an end of the specimen to permit a measurement of a current flow through each of the composite material sheets,
wherein the spacing elements are not provided between the composite material sheets at positions other than the end of the specimen, and
wherein a conductive contact part is provided at an end on a composite material sheet spacing side.

2. The specimen according to claim 1, further comprising a common conductive wire connector to which a common conductive wire allowing a current to be applied to the specimen is electrically connected at a part of the specimen where the composite material sheets are not spaced from one another.

3. The specimen according to claim 2, wherein the common conductive wire connector is a part of a surface layer of the specimen from which the conductive fibers in the composite material sheet are externally exposed.

4. The specimen according to claim 2, wherein the common conductive wire connector is located at the end of the specimen where the composite material sheets are not spaced from one another.

5. The specimen according to claim 2, further comprising:
a through-hole that penetrates the composite material sheets in a laminate direction,
wherein the common conductive wire connector includes a conductive element that is inserted into the through-hole.

6. The specimen according to claim 1, further comprising:
at least one first composite material and at least one second composite material that each comprises the composite material sheets laminated together, and are laid on a top of each other and coupled together with a conductor that penetrates both composite materials,
wherein the second composite material comprises the spacing elements.

7. The specimen according to claim 6, wherein a discrete conductive wire is enabled to be connected to each of the spaced composite material sheets on the composite material sheet spacing side of the second composite material.

8. The specimen according to claim 6, wherein the first composite material includes a common conductive wire connector to which a common conductive wire is electrically connected, the common conductive wire which allows a current to be applied to the specimen.

9. The specimen according to claim 6, wherein the first composite material comprises through-holes at predetermined intervals along a periphery of the first composite material, and conductive elements inserted respectively into the through-holes enables connection of one or more of the second composite materials.

10. The specimen according to claim 5, wherein the conductive element comprises a fastener that fastens the specimen to another element.

11. The specimen according to claim 1, wherein a spacing element of the spacing elements comprises a release film having an insulating property.

12. A specimen current measuring method for measuring a current flowing through the specimen according to claim 1, the method comprising:
electrically connecting a common conductive wire that allows a measurement current to be input, to the specimen;
electrically connecting discrete conductive wires that allow the measurement current to be picked up to the respective composite material sheets spaced from one another by the spacing elements or to some of the composite material sheets; and passing a current between the common conductive wire and the discrete conductive wires to allow either one of discrete measurement and simultaneous measurement of currents flowing through the composite material sheets in the specimen.

13. The specimen current measuring method according to claim 12, wherein conductive fibers in the composite material sheet in a surface layer of the specimen are externally exposed, and the common conductive wire is connected to an exposed part.

14. The specimen current measuring method according to claim 12, wherein a through-hole that penetrates the composite material sheets in a lamination direction is formed in the specimen, and the common conductive wire is connected to a conductive element inserted into the specimen.

15. The specimen current measuring method according to claim 14, wherein the conductive element comprises a fastener that fastens the specimen to another element.

16. The specimen current measuring method according to claim 12, wherein the common conductive wire is connected to an end of the specimen.

17. A specimen current measuring method for measuring a current flowing through the specimen according to claim 6, the method comprising:
   electrically connecting a common conductive wire that allows a measurement current to be input, to the first composite material;
   electrically connecting discrete conductive wires that allow the measurement current to be picked up to the respective composite material sheets spaced from one another by the spacing elements or to some of the composite material sheets; and
   passing a current between the common conductive wire and the discrete conductive wires to allow either one of discrete measurement and simultaneous measurement of currents flowing through the composite material sheets in the second composite material.

18. The specimen current measuring method according to claim 12, wherein the current flowing through each of the composite material sheets is measured based on either one of a current flowing through the corresponding discrete conductive wire and a voltage within a predetermined range of the discrete conductive wire.

19. The specimen current measuring method according to claim 17, wherein the current flowing through each of the composite material sheets is measured based on either one of a current flowing through the corresponding discrete conductive wire and a voltage within a predetermined range of the discrete conductive wire.

20. The specimen according to claim 1, further comprising:
   a common conductive wire connector to which a single conductive wire, allowing a current to be applied to the specimen, is electrically connected at a part of the specimen where the composite material sheets are not spaced from one another; and
   discrete conductive wire connectors at which conductive wires are enabled to be electrically connected to each of the spaced composite material sheets,
   wherein, in a longitudinal direction of an extending of the composite material sheets, the end of the specimen extends from an edge of the specimen and ending before a center of the specimen.

* * * * *